US009856287B2

(12) United States Patent
Shultz et al.

(10) Patent No.: US 9,856,287 B2
(45) Date of Patent: *Jan. 2, 2018

(54) REFOLDING PROTEINS USING A CHEMICALLY CONTROLLED REDOX STATE

(71) Applicant: AMGEN INC., Thousand Oaks, CA (US)

(72) Inventors: Joseph Edward Shultz, Binningen (CH); Roger Hart, Needham, MA (US); Ronald Nixon Keener, III, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/422,327

(22) Filed: Feb. 1, 2017

(65) Prior Publication Data
US 2017/0145049 A1 May 25, 2017

Related U.S. Application Data

(60) Continuation of application No. 14/793,590, filed on Jul. 7, 2015, which is a continuation of application No. 14/611,037, filed on Jan. 30, 2015, which is a division of application No. 12/820,087, filed on Jun. 21, 2010, now Pat. No. 8,952,138.

(60) Provisional application No. 61/219,257, filed on Jun. 22, 2009.

(51) Int. Cl.
C07K 14/00 (2006.01)
C07K 1/113 (2006.01)
C07K 1/14 (2006.01)
C07K 16/00 (2006.01)

(52) U.S. Cl.
CPC .......... *C07K 1/1136* (2013.01); *C07K 1/1133* (2013.01); *C07K 1/14* (2013.01); *C07K 14/00* (2013.01); *C07K 16/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,237,224 A | 12/1980 | Cohen et al. |
| 4,468,454 A | 8/1984 | Cohen et al. |
| 4,468,464 A | 8/1984 | Cohen et al. |
| 4,740,470 A | 4/1988 | Cohen et al. |
| 4,810,643 A | 3/1989 | Souza |
| 5,466,377 A | 11/1995 | Grandics et al. |
| 5,663,304 A | 9/1997 | Builder et al. |
| 5,849,883 A | 12/1998 | Boone |
| 5,922,846 A | 7/1999 | Cerletti et al. |
| 6,660,843 B1 | 12/2003 | Feige et al. |
| 6,808,902 B1 | 10/2004 | Treuheit et al. |
| 6,972,327 B1 | 12/2005 | Madani et al. |
| 7,138,370 B2 | 11/2006 | Oliner et al. |
| 7,435,804 B2 | 10/2008 | Kordyum et al. |
| 7,442,778 B2 | 10/2008 | Gegg et al. |
| 7,511,012 B2 | 3/2009 | Han et al. |
| 7,723,490 B2 | 5/2010 | Treuheit et al. |
| 8,906,648 B2 | 12/2014 | Butler et al. |
| 8,940,878 B2 | 1/2015 | Shultz et al. |
| 8,952,138 B2 | 2/2015 | Shultz et al. |
| 9,090,684 B2 | 7/2015 | Borrass et al. |
| 9,200,030 B2 | 12/2015 | Pizarro et al. |
| 2005/0209441 A1 | 9/2005 | Lile |
| 2006/0228329 A1 | 10/2006 | Brady et al. |
| 2007/0238860 A1 | 10/2007 | Schlegl |
| 2008/0214795 A1 | 9/2008 | Ramanan et al. |
| 2008/0260674 A1 | 10/2008 | Dietrich et al. |
| 2008/0260684 A1 | 10/2008 | Dietrich et al. |
| 2010/0267936 A1 | 10/2010 | Treuheit et al. |

FOREIGN PATENT DOCUMENTS

| | | |
|---|---|---|
| CA | 2614820 A1 | 1/2007 |
| CN | 1295580 A | 5/2001 |
| DE | 10-2005-033250 A1 | 1/2007 |
| DE | 2005/033250 A1 | 1/2007 |
| EP | 0 336 641 B1 | 10/1989 |
| EP | 0 657 466 A1 | 6/1995 |
| EP | 1 845 103 A1 | 10/2007 |
| EP | 1845103 A1 | 5/2015 |
| WO | WO 84/03711 | 9/1984 |
| WO | WO 88/08003 | 10/1988 |
| WO | WO 89/10932 | 11/1989 |
| WO | 1992/004382 A1 | 3/1992 |

(Continued)

OTHER PUBLICATIONS

United States Patent and Trademark Office Before the Patent Trial and Appeal Board. (Feb. 17, 2017). Decision Granting Institution of Inter Partes Review 37 C.F.R. § 42.108: *Apotex Inc. and Apotex Corp.* Petitioner v. *Amgen Inc. and Amgen Manufacturing Limited*, Patent Owner (Case IPR2016-01542, U.S. Pat. No. 8,952,138 B2), pp. 1-35.

Unites States District Court for the Southern District of Florida. (Dec. 11, 2015). Document 77: *Amgen Inc. and Amgen Manufacturing Limited*, Plaintiffs, v. *Apotex Inc. and Apotex Corp.*, Defendants (Case No. 15-cv-61631-JIC/BSS), pp. 1-23.

Unites States District Court for the Southern District of Florida. (Dec. 11, 2015). Document 77-4: Exhibit 4, *Amgen Inc. and Amgen Manufacturing Limited*, Plaintiffs, v. *Apotex Inc. and Apotex Corp.*, Defendants (Case No. 15-cv-61631-JIC/BSS), pp. 1-16.

(Continued)

*Primary Examiner* — Yunsoo Kim
(74) *Attorney, Agent, or Firm* — Raymond M. Doss

(57) ABSTRACT

A method of refolding proteins expressed in non-mammalian cells present in concentrations of 2.0 g/L or higher is disclosed. The method comprises identifying the thiol pair ratio and the redox buffer strength to achieve conditions under which efficient folding at concentrations of 2.0 g/L or higher is achieved and can be employed over a range of volumes, including commercial scale.

30 Claims, 8 Drawing Sheets

(56) References Cited

FOREIGN PATENT DOCUMENTS

| WO | WO93/18136 | 9/1993 |
|---|---|---|
| WO | WO 96/40912 | 12/1996 |
| WO | 1997/028272 A1 | 8/1997 |
| WO | 1999/042486 A1 | 8/1999 |
| WO | WO 2007/009950 | 1/2000 |
| WO | 2001/007477 A1 | 2/2001 |
| WO | WO 0 1/87925 | 11/2001 |
| WO | 2002/020762 A3 | 8/2002 |
| WO | WO 2004/001056 | 12/2003 |
| WO | 2004/058988 A3 | 11/2007 |
| WO | WO 2008/096370 | 8/2008 |
| WO | 2009/023270 A1 | 2/2009 |
| WO | WO2011/005488 A1 | 1/2011 |
| WO | WO2014/144903 A1 | 9/2014 |

OTHER PUBLICATIONS

Unites States District Court for the Southern District of Florida. (Jan. 8, 2016). Document 83-1: Exhibit 1, *Amgen Inc. and Amgen Manufacturing Limited*, Plaintiffs, v. *Apotex Inc. and Apotex Corp.*, Defendants (Case No. 15-cv-61631-JIC/BSS), pp. 1-19.
Document 35: Answer and Affirmative Defenses to Complaint, Counterclaim against All Plaintiffs by Apotex Corp., Apotex Inc. (Brier, Simeon) (Entered: Oct. 5, 2015), pp. 1-41.
Document 42: Plaintiff's Motion for Preliminary Injunction and Incorporated Memorandum of Law by Amgen Inc., Amgen Manufacturing Limited, pp. 1-25. Attachments: # 1 Affidavit Declaration of Robert Azelby, pp. 1-4. # 2 Affidavit Declaration of Nicholas Groombridge, pp. 1-4. # 3 Exhibit A—Apr. 17, 2015 Letter to Groombridge—Pegfilgrastim, pp. 1-2. # 4 Exhibit B—May 8, 2015 Ltr. Groombridge to Coblentz re pegfilgrastim (1)(8)(A) notice, pp. 1-3. # 5 Exhibit C—Jul. 29, 2015 N Groombridge letter to B Coblentz, pp. 1-3. # 6 Exhibit D—Aug. 24, 2015 Letter to Groombridge, pp. 1-2. # 7 Exhibit E—May 5, 2015 Order Granting Motion for an Injunction Pending Appeal, pp. 1-3. # 8 Exhibit F—Joint Stip Re Amgens Motion for Preliminary Injunction Oct. 1, 2015, pp. 1-5. # 9 Exhibit G—FDA Website Printout, pp. 1-3. # 10 Exhibit H—Jorge Mestre-Ferrandiz, et al., The R&D Cost of a New Medicine (2012), pp. 1-101. # 11 Exhibit I—Oct. 16, 2015 Order Denying Petition for En Banc Rehearing, pp. 1-3. # 12 Text of Proposed Order Proposed Order)(O'Sullivan, John) (Entered: Oct. 16, 2015), pp. 1-2.
Document 47: Apotex's Corrected Answer, Affirmative Defenses & Counterclaims to Amgen's Complaint, Oct. 23, 2015, pp. 1-42.
Document 64: Defendants Apotex's Answer, Affirmative Defenses and Counterclaims to Plaintiffs' Complaint, Dec. 1, 2015, pp. 1-45.
Document 76: Apotex's Opening Claim Construction Brief, Dec. 11, 2015, pp. 1-26.
Document 77: Amgen's Opening Claims Construction Brief, Dec. 11, 2015, pp. 1-23; Document 77-1 to Exhibit 1, U.S. Pat. No. 8,952,138, document entered on Dec. 11, 2015, pp. 1-19; Document 77-2 to Exhibit 2, U.S. Pat. No. 6,162,427, document entered Dec. 11, 2015, pp. 1-7; Document 77-3 to Exhibit 3, U.S. Pat. No. 5,824,784, document entered Dec. 11, 2015, pp. 1-31; Document 77-4 to Exhibit 4, Declaration of Richard C. Willson, Ph. D. Regarding Claim Constructions of Shultz et al., document entered Dec. 11, 2015, pp. 1-16, Document 77-5 to Exhibit A, Richard Willson CV, document entered Dec. 11, 2015, pp. 1-21; Document 77-6 to Exhibit B, Effective renaturation of denatured and reduced immunoglobulin G in vitro without assistance of chaperone, document entered on Dec. 11, 2015, pp. 1-7; Document 77-7 to Exhibit C, Effective renaturation of reduced lysosome by gentle removal of urea, document entered on Dec. 11, 2015, pp. 1-6; Document 77-8 to Exhibit D, Perspectives in Biochemistry, *Biochemistry*, document entered on Dec. 11, 2015, pp. 1-10; Document 77-9 to Exhibit E, Structural Stability of Covalently Linked GroES Heptamer: Advantages in the Formulation of Oligomeric Structure, *Science Direct*, document entered on Dec. 11, 2015, pp. 1-16.

Document 82: Brief in response to Plaintiffs' Opening Claim Construction Brief by Apotex Corp., Apotex Inc. re 11 Trial Brief, documents entered on Jan. 8, 2016, pp. 1-25. Attachments: # 1 Declaration of W. Blake Coblentz in Support of Defendants Responsive Claim Construction Brief, pp. 1-2. # 2 Exhibit A—Declaration of Anne S. Robinson, Ph.D., pp. 1-17. # 3 Exhibit B—R. Rudolph and H. Lilie, In vitro folding of inclusion body proteins). Entered: Jan. 8, 2016, pp. 1-9.
Document 83: Responsive Claim Construction Brief by Amgen Inc., Amgen Manufacturing Limited. Documents entered on Jan. 8, 2016. pp. 1-25. Attachments: # 1 Affidavit Exh. 1—Rebuttal Declaration of Richard C. Willson, pp. 1-19. # 2 Exhibit A—Feb. 23, 2012 Office Action Response, pp. 1-6. # 3 Exhibit B—'370 Patent, pp. 1-167. # 4 Exhibit C—Jan. 29, 2014 Office Action, pp. 1-8. # 5 Exhibit D—Apr. 28, 2014 Office Action Response, # 6 Affidavit Exh. 2—Rebuttal Declaration of Louis M. Pelus, pp. 1-22. # 7 Exhibit A—Pelus CV, pp. 1-49. # 8 Exhibit B—Richman, pp. 1-11. # 9 Exhibit C—Shirota, pp. 1-8. # 10 Exhibit S—Neben, pp. 1-10.
Document 89: Apotex's Reply to Plaintiffs' Responsive Claim Construction Brief. Notice by Apotex Corp., Apotex Inc. re 83 Trial Brief,, *Defendants Apotex Inc. and Apotex Corp.'s Reply to Plantiffs' Responsive Claim Construction Brief*. Documents entered on Jan. 27, 2016, pp. 1-16. Attachments: # 1 Declaration of W. Blake Coblentz in Support of Defendants' Reply to Plaintiffs' Responsive Claim Construction Brief, pp. 1-2 # 2 Exhibit A—Excerpts of deposition transcript of Richard C. Willson, III, Ph.D., pp. 1-47 # 3 A Exhibit B—Excerpts of deposition transcript of Anne Robinson, Ph.D., pp. 1-5 # 4 Exhibit C—Excerpts of deposition transcript of Louis M. Pelus, Ph.D. pp. 1-16
Document 90: Amgen's Reply Claim Construction Brief. Document entered on Jan. 27, 2016, pp. 1-15. Attachments: Exhibit 1; Videotaped Deposition of Richard C. Willson, Ph. D. Jan. 18, 2016; pp. 1-109 Exhibit 2: Videotaped Deposition of Louis M. Pelus, Ph.D. Jan. 19, 2016; pp. 1-33. Exhibit 3: Transcript of the Testimony of Videotaped Deposition of Anne Robinson, Ph. D., Jan. 20, 2016; pp. 1-60. Exhibit 4: Videotaped Deposition of David T. Scadden, M.D. Jan. 22, 2016; pp. 1-43.
Document 184: Brief Plaintiffs Supplemental Claim Construction Brief Regarding the Meaning of "Protein" in Claim 1 of the '138 Patent by Amgen Inc., Amgen Manufacturing Limited. Documents Entered: Jun. 22, 2016), pp. 1-15. Attachments: # 1 Exhibit Ex. 1—U.S. Pat. No. 8,952,138, pp. 1-19. # 2 Exhibit Ex. 5—Jan. 18, 2016 Willson Dep. Tr. (Excerpt), pp. 1-12. # 3 Exhibit Ex. 6—Jun. 22, 2012 Response to Office Action from File History of U.S. Pat. No. 8,952,138)(O'Sullivan, John), pp. 1-6.
Document 186: Trial Brief Apotex's Supplemental Claim Construction Brief in Support of Their Construction for the Term 'protein' as Used in Claim 1 of U.S. Pat. No. 8,952,138 by Apotex Corp., Apotex Inc.pp. 1-18 (Attachments: # 1 Exhibit 1 U.S. Pat. No. 8,952,138; pp. 1-19; # 2 Exhibit 6—Response to Office Action dated Jun. 22, 2012)(Brier, Simeon) (Entered: Jun. 22, 2016); pp. 1-6.
Document 244: Motion for Judgment on Partial Findings Pursuant to Fed. R. Civ. P. 52(c) by Apotex Corp., Apotex Inc. pp. 1-12, Entered: Jul. 18, 2016: Attachments # 1 Exhibit A—Pages from Trial Transcript Day 1 (Jul. 11, 2016) (Willson), pp. 1-6 # 2 Exhibit B—Pages from Trial Transcript Day 2 (Jul. 12, 2016) (Willson), pp. 1-9 # 3 Exhibit C—Pages from Trial Transcript Day 3 (Jul. 13, 2016) (Dowd), pp. 1-13. # 4 Text of Proposed Order, pp. 1
Document 247: Transcript of Bench Trial held on Jul. 11, 2016 before Judge James I. Cohn, 1-245 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).
Document 248: Transcript of Bench Trial held on Jul. 12, 2016 before Judge James I. Cohn, 1-171 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted

(56) References Cited

OTHER PUBLICATIONS

Transcript Deadline set for Aug. 22, 2016. Release of Transcript Restriction set for Oct. 20, 2016. (Shires, Karl) (Entered: Jul. 18, 2016).
Document 249: Transcript of Bench Trial held on Jul. 13, 2016 before Judge James I. Cohn, 1-61 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).
Document 250: Transcript of Bench Trial held on Jul. 14, 2016 before Judge James I. Cohn, 1-242 pages, Court Reporter: Karl Shires, 954-769-5496 / Karl_Shires@flsd.uscourts.gov. Transcript may be viewed at the court public terminal or purchased by contacting the Court Reporter/Transcriber before the deadline for Release of Transcript Restriction. After that date it may be obtained through PACER. Redaction Request due Aug. 11, 2016. Redacted Transcript Deadline set for Aug. 22, 2016. Release of Transcript Restriction set for Oct. 20, 2016. (Shires, Karl) (Entered: Jul. 18, 2016).
Document 254: Response in Opposition re 244 Motion for Judgment on Partial Findings Pursuant to Fed. R. Civ. P. 52(c) filed by Amgen Inc., Amgen Manufacturing Limited. Replies due by Aug. 15, 2016; pp. 1-20.
Document 259: Mandate of US Federal Circuit (certified copy) Affirm Judgment/ Order of the district court with courts opinion re 72 Notice of Appeal, filed by Apotex Corp., Apotex Inc. ; Date Issued: Aug. 11, 2016 ; US Federal Circuit Case No. 16-1308 (amb) (Entered: Aug. 11, 2016); pp. 1-26.
Document 260: Reply to Response to Motion re 244 Motion for Judgment on Partial Findings Pursuant to Fed. R. Civ. P. 52(c) filed by Apotex Corp., Apotex Inc. pp. 1-11; Attachments: # 1 Exhibit 1—Trial Transcript Day 2 (Jul. 12, 2016) (Willson), pp. 1-7. # 2 Exhibit 2—Trial Transcript Day 3 (Jul. 13, 2016) (Dowd), pp. 1-4. # 3 Exhibit 3—Trial Transcript Day 4 (Jul. 14, 2016) (Robinson), pp. 1-4. # 4 Exhibit 4—Trial Transcript Day 5 (Jul. 18, 2016), pp. 1-3.
Document 268: Final Judgment Signed by Judge James I. Cohn on Sep. 6, 2016. (tpl) Notice: If there are sealed documents in this case, they may be unsealed after 1 year or as directed by Court Order, unless they have been designated to be permanently sealed. See Local Rule 5.4 and Administrative Order 2014-69. (Entered: Sep. 6, 2016); pp. 1-5.
http://chemistry.umeche.maine.edu/CHY431/Ribo-fold.jpg, 2016.
UniProtKB—Q6EBC2 (IL31_HUMAN) UniProt (2016), pp. 1-8 http://www.uniprot.org/uniprot/Q6EBC2.
UniProtKB—Q6EAL8 (IL31_MOUSE) UniProt (2016), pp. 1-7.
IUPAC Gold Book—dalton (2016). Amgen Exhibit 2014: *Apotex Inc. et al. V. Amgen Inc. et al.*, (IPR2016-01542), pp. 1.
Protein Structure Graphic http://pubs.rsc.org/services/images/RSCpubs.ePlatform.Service.FreeContent.ImageService.svc/ImageService/Articleimage/2014/TB/c4tb00168k/c4tb00168k-f2_hi-res.gif.
Protein Data Bank, Hen Egg White Lysozyme, http://www.rcsb.org/pdb/explore/explore.do?structureId=193L; http://www.rcsb.org/pdb/explore/remediatedSequence.do?structureId=193L.
DeBernadez Clark, Eliana, *Refolding of recombinant proteins*, Current Opinion in Biotechnology, vol. 9, pp. 157-163 (1998).
Kamau, Samuel M. et al. (2010). Alpha-Lactalbumin: Its Production Technologies and Bioactive Peptides. *Comprehensive Reviews in Food Science and Food Safety*, pp. 197-212, vol. (9).
Lehninger, Albert L. (1982). Chapter 17: Electron Transport, Oxidative Phosphorylation, and Regulation of ATP production. *Principles of Biochemistry*. New York, New York: Worth Publishers, Inc., pp. 1-46.

Lu et al. (May 5, 1992). Folding and Oxidation of Recombinant Human Granulocyte Colony Stimulating Factor Produced in *Escherichia coli*: Characterization of the disulfide-reduced intermediates and cysteine→Serine Analogs. *The Journal of Biological Chemistry*, pp. 8770-8777.
Phillips, David C. (1966). The Three-dimensional Structure of an Enzyme Molecule. Scientific American, pp. 78-90.
Schrodel and De Marco (May 31, 2015). Characterization of the aggregates formed during recombinant protein expression in bacteria. *BMC Biochemistry*. DOI: 10.1186/1471-2091-6-10, pp. 1-11.
Slanger, Charles J. et al. (1999). Use of Mass Spectrometry to Rapidly Characterize the Heterogeneity of Bovine α-Lactalbumin. *Department of Product Technology BIZO Food Research* vol. (47), pp. 4549-4556.
Yamaguchi, Satoshi, et al. (2013). Protein refolding using chemical refolding additives. *Biotechnology Journal*, v (8), pp. 17-31.
United States Patent and Trademark Office Before the Patent Trial and Appeals Board. (Nov. 23, 2016). Patent Owners' Preliminary Response: *Apotex Inc. and Apotex Corp.* Petitioners v. *Amgen Inc. and Amgen Manufacturing Limited*, Patent Owners (Case IPR2016-01542, U.S. Pat. No. 8,952,138), pp. i-v, pp. 1-51.
United States Patent and Trademark Office Before the Patent Trial and Appeals Board. (Aug. 29, 2016). Patent Owner's Mandatory Notices: *Apotex Inc. and Apotex Corp.* Petitioners v. *Amgen Inc. and Amgen Manufacturing Limited*, Patent Owners (Case IPR2016-01542, U.S. Pat. No. 8,952,138), pp. 1-3.
United States Patent and Trademark Office Before the Patent Trial and Appeals Board. (Aug. 25, 2016). Notice of Filing Date Accorded to Petition and Time for Filing Patent owner Preliminary Response: *Apotex Inc. and Apotex Corp.* Petitioner v. *Amgen Inc. and Amgen Manufacturing Limited*, Patent Owner (Case IPR2016-01542, U.S. Pat. No. 8,952,138), pp. 1-5.
United States Patent and Trademark Office Before the Patent Trial and Appeals Board. (Aug. 25, 2016). Petition for Inter Partes Review of U.S. Pat. No. 8,952,138 Under 35 U.S.C. §§ 3.11-319 and 37 C.F.R. §§ 42.1-.80, 42.100-.123: *Apotex Inc. and Apotex Corp.* Petitioners v. *Amgen Inc. and Amgen Manufacturing Limited*, Patent Owner (Inter Partes Review No. IPR2016-01542), pp. i-viii, pp. 1-69.
United States Patent and Trademark Office Before the Patent Trial and Appeals Board. (Aug. 29, 2016). Updated Mandatory Notices for Patent Owners: *Apotex Inc. and Apotex Corp.* Petitioners v. *Amgen Inc. and Amgen Manufacturing Limited*, Patent Owners (Case IPR2016-01542, U.S. Pat. No. 8,952,138), pp. 1-4.
United States Patent and Trademark Office Before the Patent Trial and Appeal Board. (Nov. 23, 2016). Declaration, pp. 1-81, Curriculum Vitae of Richard C. Willson, PhD.pp. 1-7: *Apotex Inc. and Apotex Corp.* v. *Amgen Inc. and Amgen Manufacturing Limited* (Inter Partes Review No. IPR2016-01542, U.S. Pat. No. 8,952,138).
United States Patent and Trademark Office Before the Patent Trial and Appeal Board. (Aug. 5, 2016). Declaration pp. 1-74, Curriculum Vitae of Anne S Robinson, PhD. pp. 1-7, Appendix A, pp. 1-4: *Apotex Inc. and Apotex Corp.* v. *Amgen Inc. and Amgen Manufacturing Limited* (Inter Partes Review No. IPR2016-01542).
United States Patent and Trademark Office. *Notice of Allowance and Fees Due*, U.S. Appl. No. 12/820,087, pp. 1-3, 2004.
United States Patent and Trademark Office. (Jan. 9, 2012). Information Disclosure Statement by Applicant, pp. 1-2.
Unites States District Court Southern District of Florida. (Apr. 7, 2016). Claim Construction Order, Document 119: *Amgen Inc. and Amgen Manufacturing Limited*, Plaintiffs, v. *Apotex Inc. and Apotex Corp.*, Defendants (Case No. 15-61631-CIV-Cohn/Seltzer), pp. 1-12.
Unites States District Court Southern District of Florida. (Sep. 6, 2016). Findings of Fact and Conclusions of Law, Document 267: *Amgen Inc. and Amgen Manufacturing Limited*, Plaintiffs v. *Apotex Inc. and Apotex Corp.*, Defendants (Case No. 15-61631-CIV-COHN/SELTZER, Consolidated With 15-62081-CIV-COHN/SELTZER, pp. 1-30).

(56) References Cited

OTHER PUBLICATIONS

Unites States District Court for the Southern District of Florida. (Jul. 18, 2016). Partial Findings Regarding Apotexs Assertion of Invalidity of the 138 Patent. Signed by Judge James I. Cohn. Document 245: *Amgen Inc. and Amgen Manufacturing Limited*, Plaintiffs, v. *Apotex Inc. and Apotex Corp.*, Defendants (Case No. 15-cv-61631-JIC), pp. 1-5.
Gottschalk, U. "Filtration and Purification in the Biopharmaceutical Industry," ebook CRC Press 2007, eds. Maik W. Jornitz and Theodore H. Meltzer, 2$^{nd}$ ed, pp. 459-495.
US District Court, Southern District of Florida; Case No. 15-61631-CIV-COHN (consolidated with 15-62081-CIV-COHN) *Amgen Inc. and Amgen Manufacturing Limited* v. *Apotex Inc. and Apotex Corp*; Defendants *Apotex Inc. and Apotex Corp.*; Invalidity Contentions; Dec. 1, 2015.
US District Court, Southern District of Florida; Case No. 15-cv-61631-JIC/BSS, *Amgen Inc. and Amgen Manufacturing Limited* v. *Apotex Inc. and Apotex Corp*; Defendants *Apotex Inc. and Apotex Corp.*; "Pegfil—Invalidity Contentions" Oct. 19, 2015.
Appendix A: Prior Art Chart for U.S. Pat. No. 8,952,138; Pegfil Invalidity Claim Chart 2015.
Hevehan and Clark, "Oxidative Renaturation of Lysozyme at High Concentrations," Biotechnology and Bioengineering, 1996, 54(3): 221-230.
Hakim and Benhar, "Inclonals," mAbs, published online May 1, 2009, 1:3, 281-287.
Whitford, "Proteins: Structure and Function," Sep. 1, 2005.
http://chemistry.umeche.maine.edu/CHY431/Ribo-fold.jpg, 2015.
Johnson, "Human insulin from recombinant DNA technology". Science (1983) 219 (4585): 632-637.
Vallejo et al. "Strategies for the recovery of active proteins through refolding of bacterial inclusion body proteins," Microbial Cell Factories (2004) 3, 1-12.
Neubauer et al. "Protein inclusion bodies in recombinant bacteria. Inclusions in Prokaryotes." Microbiology Monographs Edited by: Shively JM. Springer; (2006) 237-292.
https://www.profacgen.com/inclusion-body-purification-protein-refolding.htm, 2016.
Georgiou and Valax, "Isolating Inclusion Bodies from Bacteria", Chapter 3 in Methods in Enzymology, vol. 309, p. 48-58 (1999) Academic Press.
Palmer and Wingfield "Preparation and Extraction of Insoluble (Inclusion-Body) Proteins from *Escherichia coli*" Curr Protoc Protein Sci. Nov. 2004; Chapter: Unit-6.3. doi:10.1002/0471140864. ps0603s38.
Shortle et al., "Clustering of Low-Energy Conformations Near the Native Structures of Small Proteins," Proc Natl Acad Sci (1998) 95, 11158-62.
Panda, "Bioprocessing of Therapeutic Proteins from the Inclusion Bodies of *Escherichia coli*" Adv Biochem Engin/Biotechnol (2003) 85: 43-93.
Vincentelli, "High-throughput automated refolding screening of inclusion bodies," Protein Science (2004) 13:2782-2792.
Willis et al., "Investigation of protein refolding using a fractional factorial screen: A study of reagent effects and interactions." Protein Science (2005) 14(7), 1818-1826.
Jungbauer and Kaar "Current status of technical protein refolding," Journal of Biotechnology 128 (2007) 587-596.
Ferrer-Miralles et al. "Microbial factories for recombinant pharmaceuticals" Microbial Cell Factories (2009) 8:17.
Graumann and Premsaller, "Manufacturing of recombinant therapeutic proteins in microbial systems," Biotech J. (2006) 1:164-186.
Xie and Wetlaufer, "Control of aggregation in protein refolding: The temperature-leap tactic," Protein Science (1996) 5:517-523.
Puri, "Refolding of recombinant porcine growth hormone in a reducing environment limits in vitro aggregate formation," FEBS (1991) vol. 292, No. 1.2, 187-190.
Ejima, "High yield refolding and purification process for recombinant human interleukin-6 expressed in *Escherichia coli*," Biotechnology and Bioengineering (1999) vol. 62, No. 3, 301-310.

Patra et al., "Optimization of inclusion body solubilization and renaturation of recombinant human growth hormone from *Escherichia coli*," Protein Expression and Purification (2000) 18, 182-192.
Mannall et al., "Factors Affecting Protein Refolding Yields in a Fed-Batch and Batch-Refolding System," Biotechnology and Bioengineering, (2007) vol. 97, No. 6, 1523-1534.
Misawa and Kumagai "Refolding of Therapeutic Proteins Produced in *Escherichia coli* as Inclusion Bodies" Biopoly (1999) 51: 297-307.
Park et al., "A Divalent Recombinant Immunotoxin Formed by a Disulfide Bond between the Extension Peptide Chains," Mol. Cells (2001) vol. 12, No. 3, 398-402.
EnbrelTM (etanercept) label, Nov. 1998.
Bolado, "Amgen Opens Trial in Fight Over Neulasta Generic," Law360, Jul. 11, 2016 (http://www.law360.com/articles/814748/amgen-opens-trial-in-fight-over-neulasta-generic).
Protein Data Bank, Hen Egg White Lysozyme, http://www.rcsb.org/pdb/explore/explore.do?structureId=193L; http://www.rcsb.org/pdb/explore/remediatedSequence.do?structureId=193L, 2016.
Maurer et al., "Folding and aggregation of a multi-domain engineered immunotoxin," Biochemical Engineering Journal (2013) 81:8-14.
Sereikaite et al. "Production of recombinant mink growth hormone in *E. coli*," Appl Microbiol Biotechnol (2007) 74:316-323.
Shimamoto et al., "Peptibodies: A flexible alternative format to antibodies," mAbs (Sep./Oct. 2012) 4:5, 586-591.
http://pubs.rsc.org/services/images/RSCpubs.ePlatform.Service. FreeContent.ImageService.svc/ImageService/Articleimage/2014/TB/c4tb00168k/c4tb00168k-f2__hi-res.gif.
Bowden et al., "Structure and morphology of protein inclusion bodies in *Escherichia coli*" Bio/Tech (1991) 9:725-730.
Weiss et al. "Principles, Approaches, and Challenges for Predicting Protein Aggregation Rates and Shelf Life" J Pharm Sci. Apr. 2009; 98(4):1246-77.
Ventura and Villaverde "Protein quality in bacterial inclusion bodies" Trends in Biotechnology vol. 24 No. 4 Apr. 2006.
Cowley & Mackin, "Expression, purification and characterization of recombinant human proinsulin," FEBS Lett 402:124-130 (1997).
Rudolph & Lilie, "In vitro folding of inclusion body proteins," FASEB J. 10: 49-56 (1996).
Creighton, T.E., "Renaturation of the reduced bovine pancreatic trypsin inhibitor," J. Mol. Biol. 87: 563-577, (1974).
Stöckel, J. et al., "Pathway of detergent-mediated and peptide ligand-mediated refolding of heterodimeric class II major histocompatibility complex (MHC) molecules," Eur J. Biochem 248: 684-691 (1997).
St. John et al., "High pressure refolding of recombinant human growth hormone from insoluble aggregates. Structural transformations, kinetic barriers, and energetics," J. Biol. Chem. 276(50): 46856-63 (2001).
Lilie, Schwarz & Rudolph, "Advances in refolding of proteins produced in *E. coli*," Current Opinion in Biotechnology 9(5): 497-501 (1998).
Tran-Moseman, Schauer & Clark, "Renaturation of *Escherichia coli*-derived recombinant human macrophage colony stimulating factor," Protein Expression and Purification 16(1): 181-189 (1999).
Darby, N.J. et al., "Refolding of bovine pancreatic trypsin inhibitor via non-native disulphide intermediates," J. Mol. Biol. 249(2): 463-477, (1995).
Snyder et al., "Characterization of DC-SIGN/R Interaction with Human Immunodeficiency Virus Type 1 gp 120 and ICAM Molecules favors the receptor's role as an antigen-capturing rather than an adhesion receptor," J. Virology 79(8):4589-4598, Apr. 2005.
Javaherian, K. et al., "Laminin Modulates Morphogenic Properties of the Collagen XVIII Endostatin Domain," J. Biol. Chem. 277(47):45211-45218, Nov. 22, 2002.
GE Healthcare Instructions 71-7089-00AE: Affinity media, Protein A Sepharose CL-4B, p. 1-8, Mar. 2006. (Cited in JP Office action http://eclub.biomart.cn/sites/eclub.biomart.cn/themes/aktaclub/Files/71708900AE_UM_Protein_A_Sepharose_CL-4B.pdf, Mar. 2006).

(56) References Cited

OTHER PUBLICATIONS

GE Healthcare Instructions 71-5002-60 AE: Ion exchange chromatography; Q Sepharose XL, XL virus licensed, SP Sepharose XL, pp. 1-16, Feb. 2006 (cited in JP Office action as D6https://www.gelifesciences. com/gehcls_images/GELS/Related%20Content/Files/1314723116657/litdoc71500260AE_20110830185637.pdf, Feb. 2006).

Pavlinkova et al., Charge-Modified Single Chain Antibody Constructs of Monoclonal Antibody CC4: Generation, Characterization, Pharmokinetics and Biodistribution Analysis (Nuclear Med. Biol., vol. 26, pp. 27-34, 1999.

Ronnmark et al, "Construction and characterization of affibody-Fc chimeras produced in *Escherichia coli*" (Journal of Immunological Methods, 261:199-211, 2002).

Tengliden, "Development of Cleaning-in-Place Procedures for Protein A Chromatography Resins Using Design of Experiments and High Throughput Screening Technologies", Masters Thesis, Linkoping University, Feb. 2008).

Arvidsson, P. et al., "Direct chromatographic capture of enzyme from crude homogenate using immobilized metal affinity chromatography on a continuous supermacroporous adsorbent," Journal of Chromatography 986 (2): 275-290 (2003).

Ling et al., "Integration of mechanical cell disruption and fluidised bed recovery of G3PHD from unclarified disrupted 2 yeast: a comparative study of the performance of unshielded and polymer shielded dye-ligand chromatography systems," J. Biotech. 119(4): 436-448 (2005).

Fischer, B. et al., "Isolation renaturation and formation of disulfide bonds of eukaryotic proteins expressed in *Escherichia coli* as inclusion bodies," Biotech. and Bioengineering, 41(1): 3-13 (1993).

Ford et al., "Affinity purification of novel bispecific antibodies recognising carcinoembryonic antigen and doxorubicin,"J. Chromatogr. B, 754: 427-435 (2001).

Shukla et al., "Downstream processing of monoclonal antibodies—Application of platform approaches," Journal ofChromatography B, 848(1 ):28-39 (2007).

Wang et al., "Perturbation of the antigen-binding site and staphylococcal protein A-binding site of IgG beforesignificant changes in global conformation during denaturation: an equilibrium study," Biochem. J. 325(Part 3):707-710 (1997).

Hasemann & Capra, "Immunoglobulins: Structure and Function," in William E. Paul, ed., Fundamental Immunology, Second Edition, 209, 210-218 (1989).

Ostrove, "Affinity Chromatography: General Methods," Guide to Protein Purification, Methods in Enzymology 182: 371-379 (1990).

Devereux et al., "A comprehensive set of sequence analysis programs for the VAX," Nucleosides, nucleotides & nucleic acids: Nucl. Acids Res. 12: 387-389 (1984).

Gribskov and Burgess, "Sigma factors from *E. coli*, B. subtilis, phage SP01, and phage T4 are homologous proteins," Nucl. Acids Res. 14: 6745 (1986).

Gulich, Susanne, et al., "Protein engineering of an IgG-binding domain allows milder elution conditions during affinity chromatography," J. Biol. 76, Issues 2-3, pp. 233-244 (2000).

Ostrove, "Affinity Chromatography: General Methods," Guide to Protein Purification, Methods in Enzymology 182: 357-371 (1990).

Stoscheck, C., "Quantitation of Protein," Guide to Protein Purification, Methods in Enzymology 182: 50-68 (1990).

Vola et al., "Recombinant proteins Land LG. Two new tools for purification of murine antibody fragments," CellBiophys. 24-25: 27-36 (1994).

Aybay and Imir, "Development of a rapid, single-step procedure using protein G affinity chromatography to deplete fetal 12 calf serum of its IgG and to isolate murine IgG1 monoclonal antibodies from supernatants of hybridoma cells," Int'l J. Immunol. Methods 233(1-2): 77-81 (2000).

Ejima, Daisuke, et al., Effective elution of antibodies by arginine and arginine derivatives in affinity column chromatography, Analytical Biochem. 345250-257 (2005).

Arakawa, Tsutomu et al., "Elution of antibodies from a Protein-A column by acqueous arginine solutions," Protein Express & Purif., 36: 244-248 (2004).

Miller, Timothy et al., The rapid isolation of ribonuclease-free immunoglobulin G by protein A—sepharose affinity chromatography, J. Immun. Methods 24: 111-125 (1978).

Singh et al., "Solubilation and Refolding of Bacteria Inclusion Body Proteins," J. Bioscience and Bioengineering, vol. 99(4), pp. 3o3-310 (2005).

DeBernadez Clark, Eliana, "Refolding of recombinant proteins," Current Opinion in Biotechnology, vol. 9, pp. 157-163 (1998).

DeBernadez Clark, Eliana, "Protein Refolding for industrial processes," Current Opinion in Biotechnology, vol. 12, pp. 202-207 (2001).

De Berndez Clark, Eliana, et al. "Oxidative Renaturation of Hen Egg-White Lysozyme. Folding vs aggregation."Biotechnol. Prog. 14: 47-57 (1998).

Videotaped Deposition of Anne Skaja Robinson, IPR 2016-01542, United States Patent and Trademark Office Before the Patent and Appeal Board, May 8, 2017, pp. 1-72.

Second Declaration of Richard C. Willson, Ph.D., IPR 2016-01542, United States Patent and Trademark Office before the Patent Trial and Appeal Board, May 22, 2017, pp. 1-65.

Contracting the Protein With a Refold Buffer, Slide, Amgen Exhibit 2018, IPR 2016-01542, pp. 1.

Patent Owner's Response, Case IPR 2016-01542, U.S. Pat. No. 8,952,138, United States Patent and Trademark Office Before the Patent Trial and Appeal Board, May 22, 2017, pp. 1-78.

Patent Owner's Motion to Seal, IPR 2016-01542, Date May 22, 2017, pp. 1-6.

Joint Motion for Entry of Stipulated Protective Order, IPR 2016-01542, U.S. Pat. No. 8,952,138, United States Patent and Trademark Office before the Patent Trial and Appeal Board, dated May 22, 2017, pp. 1-22.

Benham, et al. Disulfide bonding patterns and protein topologies, Protein Science (1993), 2, 41-54. Cambridge University Press, pp. 1-14.

Wilson, Richard C. Updated Resume, Amgen Exhibit 2053, IPR 2016-01542, pp. 1-7.

Arnold L. Demain, Pretti Vaishnav, Production of recombinant proteins by microbes and higher organisms, Biotechnology Advances, 27 (2009) pp. 297-306, https://www.researchgate.net/publication/26270590.

Tatsumi E. et al. Denatured State of Ovalbumin in High Concentrations of Urea as Evaluated by Disulfide Rearrangement Analysis, The Journal of Biological Chemistry, vol. 269, No. 45, Issue of Nov. 11, pp. 28062-28067, 1994.

Radford S. et al., The folding of hen lysozyme involves partially structured intermediates and multiple pathways, Amgen Exhibit 2049, IPR 2016-01542, pp. 1-6.

Finke J., et al. Aggregation Events Occur Prior to Stable Intermediate Formation during Refolding of Interleukin 1β. Biochemistry 2000, 39, 575-583.

Booth D., Instability, unfolding and aggregation of human lysozyme variants underlying amyloid fibrillogenesis, Nature, vol. 385, Feb. 27, 1997, Amgen Exhibit 2047, IPR 2016-01542, pp. 1-7.

Jiang X., et al. The V122I cardiomyopathy variant of transthyretin increases the velocity of rate-limiting tetramer dissociation, resulting in accelerated amyloidosis, Department of Chemistry and The Skaggs Institute of Chemical Biology, pp. 1-6.

Darby, N. et al., Refolding of Bovine Pancreatic Trypsin Inhibitor via Non-native Disulphide Intermediates, J. Mol. Biol. (1995) 249, 463-477.

Tobacman, L. et al., The Kinetics of Actin Nucleation and Polymerization, The Journal of Biological Chemistry, vol. 258, No. 5, Issue of Mar. 10, pp. 3207-3214, 1983, pp. 1-9.

Ferrone, F., Analysis of Protein Aggregation Kinetics, Methods of Enzymology, vol. 309, Amgen Exhibit 2043, IPR 2016-01542, pp. 1-19.

Matagne, A., The folding process of hen lysozyme: a perspective from the "new view", CMLS, Cell. Mil. Life Sci. 54 (1998) 363-371.

(56) References Cited

OTHER PUBLICATIONS

Buswell, M., et al., A New Kinetic Scheme for Lysozyme Refolding and Aggregation Department of Chemical Engineering, University of Cambridge, Pembroke Street, Cambridge CB2 3RA United Kingdom, DOI: 10.1002/bit.10705, accepted Mar. 3, 2003, Amgen Exhibit 2042, pp. 1-11.

Matthews, R. Pathways of Protein Folding, Department of Chemistry, Pennsylvania State University, University Park, Pennsylvania 16802, Annu. Rev. Biochem. 1993, 62:653-83, Amgen Exhibit 2039, pp. 1-33.

Svensson, M.et al., Conversion of α-lactalbumin to a prtein inducing apoptosis, Department of Microbiology, Immunology, and Glycobiology, Institute of Laboratory Medicine, Lund University, Solvegata 23, S-223, 62 Lund, Sweden, PNAS, Apr. 11, 2000, vol. 97, No. 8, 4221-4226, Amgen Exhibit 2040, pp. 1-6.

Permyakov E. et al, α-lactalbumin: structure and function, FEBS Letters 473 (2000) 260-274, Amgen Exhibit 2038, pp. 1-6.

Ewbank, J. et al., Structural Characterization of the Disulfide Folding Intermediates of Bovine α-Lactalbumin, Biochemistry 1993, 32, 3694-3707, Amgen Exhibit 2036, pp. 1-14.

Georgiou, G., Isolating Inclusion Bodies from Bacteria, In Vivo Protein Deposition, Amgen Exhibit 2034, pp. 1-11.

Darby, N., Feature-blind grammar and dysphasia, Scientific Correspondence, Nature, vol. 344, Apr. 19, 1990, Amgen Exhibit 2035, pp. 1-2.

Maachupalli-Reddy, J. et al., Effect of Inclusion Body Contaminants on the Oxidative Renaturation of Hen Egg White Lysozyme, Biotechnol. Prog. 1997, 13, 144-150, Amgen Exhibit 2033, pp. 1-7.

Chow, Michelle, et al., REFOLD: An analytical database of protein refolding methods, Science Direct, Protein Expression & Purification, Received Jun. 14, 2005, and in revised form Jul. 19, 2005, available online Aug. 15, 2005, Amgen Exhibit 2032, pp. 1-6.

Eiberle, M., Technical refolding of proteins: Do we have freedom to operate? Biotechnol. J. 2010, 5, 547-559, Amgen Exhibit 2030, pp. 1-13.

Lilie H. et al., Advances in refolding of proteins produced in *E. coli*, Current Opinion in Biotechnology, 1998, 9: 497-501, Amgen Exhibit 2031, pp. 1-5.

Declaration of Anne S. Robinson, Ph.D. in support of defendants' opening claim construction brief, Dated Dec. 11, 2015, Amgen Exhibit 2029, IPR 2016-01542, pp. 1-42, United States District Court Southern District of Florida.

Transcript of Bench Trial Proceedings Before the Honorable James I. Cohn U.S. District Judge, dated Jul. 14, 2016, Fort Lauderdale, Florida, Amgen Exhibit 2028, pp. 1-242.

Padhi D. et al., Pharmacological Inhibition of Myostatin and Changes in Lean Body Mass and Lower Extremity Muscle Size in Patients Receiving Anddrogen Deprivation Therapy for Prostate Cancer, JCEM Online, Hot Topics in Translational Endocrinology—Endocrine Research, J Clin Endcrinol Metab, Oct. 2014, 99(10)E19671975, ISSN Online 1945-7197, Accepted Jun. 2, 2014, First Published Online Jun. 27, 2014, Amgen Exhibit 2026, pp. 1-9.

Declaration of Roger A. Hart, Ph.D., IPR2016-01542, United States Patent and Trademark Office Before the Patent Trial and Appeal Board, Amgen Exhibit 2021, pp. 1-39.

Defendants' Invalidity Contentions, Case No. 3:14-cv-04741-RS, United States District Court Northern District of California San Francisco Division, pp. 1-186.

Edward R. Barnhart, Physicians' Desk Reference, 46th Ed., Neupogen®, 595-598.

R.L. Basser et al., Adjuvant Treatment of High-Risk Breast Cancer Using Multicycle High-Dose Chemotherapy and Filgrastim-mobilized Peripheral Blood Progenitor Cells, Clin. Cancer Res.1:715-721 (Jul. 1995).

C.G. Begley et al., G-CSF Mobilised Progenitor Cells in Autologous Transplantation: In Vitro and In Vivo Aspects, J. Nutr. Sci. Vitaminol. (Tokyo). Spec No.368-71 (1992).

M. Fukuda et al., Autotransplantation of Peripheral Blood Stem Cells Mobilized by Chemotherapy and Recombinant Human Granulocyte Colony-Stimulating Factor in Childhood Neuroblastoma and Non-Hodgkin's Lymphoma, British J. Haematology 80:327-331 (1992).

G. Morstyn et al., Treatment of Chemotherapy-Induced Neutropenia by Subcutaneously Administered Granulocyte Colony-Stimulating Factor With Optimization of Dose and Duration of Therapy, J. Clin. Onc., 7(10):1554-1562 (1989).

S. Neben et al., Mobilization of Hematopoietic Stem and Progenitor Cell Subpopulations from the Marrow to the Blood of Mice Following Cyclophosphamide and/or Granulocyte Colony-Stimulating Factor, Blood, 81(7):1960-1967 (1993).

R. Pettengell et al., Transplantation Potential of Hematopoietic Cells Released Into the Circulation During Routine Chemotherapy for Non-Hodgkin's Lymphoma, Blood, 82(7):2239-2248 (1993).

W.P. Sheridan et al., Effect of Peripheral-Blood Progenitor Cells Mobilised by Filgrastim (G-CSF) on Platelet Recovery After High-Dose Chemotherapy, The Lancet 339:640-644 (1992).

W.P. Sheridan, Transplantation of Mobilized Peripheral Blood Stem Cells: Role of Filgrastim, J. Hematotherapy 3:349-352 (1994).

Tsunemichi Shirota et al., Cyclophosphamide-induced Alterations of Bone Marrow Endothelium: Implications in Homing of Marrow Cells After Transplantation, Exp. Hematol.19:369-373 (1991).

M.E.H.M. Van Hoef et al., Dose-Escalating Induction Chemotherapy Supported by Lenograstim Preceding High-Dose Consolidation Chemotherapy for Advanced Breast Cancer: Selection of the Most Acceptable Regimen to Induce Maximal Tumor Response and Investigation of the Optimal Time to Collect Peripheral Blood Progenitor Cells for Haematological Rescue After High-Dose Consolidation Chemotherapy, Ann. Oncol. 5:217-224 (1994).

Defendants' Invalidity Contentions, Case No. 3:16-cv-02581-RS, United States District Court Northern District of California San Francisco Division, pp. 1-119.

E. Breen et a l. On the Mechanism of Mitochondrial Uncoupling Protein 1 Function, J. Biol. Chem., 281 (4):2114-2119 (2006).

M. Jaburek & K. D. Garlid. Reconstitution of Recombinant Uncoupling Proteins, J. Biol. Chem., 278 (28):25825-25831 (2003).

D. Johnson et a l. Refolding, Purification, and Characterization of Human Erythropoietin Binding Protein Produced in *Escherichia coli*. Protein Expression and Purification 7:104-113 (1996).

K.Y. Kang et al. Purification and Characterization of a Recombinant Anti-Angiogenic Kringle Fragment Expressed in *Escherichia coli*: Purification and Characterization of a Tri-Kringle Fragment from Human Apolipoprotein (a), Protein Expression and Purification; 45:216-225 (2006).

Novagen, Inc. Protein Refolding Kit ("Novagen"), pp. 1-9, 1997-1998.

X.D. Wang et a l. Perturbation of the antigen-binding site and staphylococcal Protein A—binding site of IgG before significant changes in global conformation during denaturation: an equilibrium study, Biochem. J. 325:707-710 (1997).

M. Yamasaki et a l. Purification and Characterization of Recombinant Human Granulocyte Colony-Stimulating Factor (rhG-CSF) Derivatives: KW-2228 and Other Derivatives, Biosci. Biotechnol. Biochem. 62(8):1528-1534 (1998).

GE Healthcare Life Sciences "Streamline SP, 300 ml" (http://www.gelifesciences.com/webapp/wcs/stores/servlet/catalog/en/GELifeSciences/prod . . . ; date retrieved Dec. 9, 2015, SDZ(56)0259126, pp. 1); current version of webpage: http://www.gelifesciences.com/webapp/wcs/stores/servlet/productById/en/GELifeSciences-us/17099301(date retrieved Jul. 17, 2017).

GE Healthcare, Instructions 71-7100-00AC Ion Exchange, DEAE Sephacel, SDZ(56)0259118, pp. 1-8.

Tosoh Bioscience GmbH, Toyopearl DAEAE-650, http://www.separations.eu.tosohbioscience.com/ProductsPrinterFriendlyTemplate.aspx?N . . . ; date retrieved Dec. 9, 2015, pp. 1-2, SDZ(56)0259127; current version of webpage: http://www.separations.eu.tosohbioscience.com/solutions/process-media-products/by-mode/ion-exchange/anion-exchange/toyopearl-deae-650.

Gabriela Pavlinkova et al., Charge-Modified Single Chain Antibody Constructs of Monoclonal Antibody CC49: Generation, Characterization, Pharmacokinetics, and Biodistribution Analysis, 26 Nuclear Med. & Biology.

(56) References Cited

OTHER PUBLICATIONS

Dana L. Johnson, et al., *Refolding, Purification, and Characterization of Human Erythropoietin Binding Protein Produced in Escherichia coli*, 7 Protein Expression and Purification 104 (1996).
Chaozhan Wang at al., *Refolding Recombinant Human Granulocyte Colony Stimulating Factor Expressed by E. coli*, 4 BioProcess Int'l 48 (2006).
Chaozhan Wang et al., *Renaturation with Simultaneous Purification of rhGCSF from Escherichia coli by Ion Exchange Chromatography*, 21 Biomedical Chromatography 1291 (2007).
Reply Declaration of Anne S. Robinson, Ph.D.; United States Patent and Trademark Office Before the Patent Trial and Appeal Board, *Apotex Inc. and Apotex Corp.* v. *Amgen Inc. and Amgen Manufacturing Limited*, Inter Partes Review No. IPR2016-01542 U.S. Pat. No. 8,952,138, pp. 1-45; Aug. 21, 2017.
Reply to Patent Owner Response; United States Patent and Trademark Office Before the Patent Trial and Appeal Board, *Apotex Inc. and Apotex Corp.* v. *Amgen Inc. and Amgen Manufacturing Limited*, Inter Partes Review No. IPR2016-01542 U.S. Pat. No. 8,952,138, pp. 1-36; Aug. 21, 2017.

REFOLDING PROTEINS USING A CHEMICALLY CONTROLLED REDOX STATE

This application is a continuation of pending U.S. patent application Ser. No. 14/793,590, filed on Jul. 7, 2015; which is a continuation of pending U.S. patent application Ser. No. 14/611,037, filed on Jan. 30, 2015; which is a divisional of U.S. patent application Ser. No. 12/820,087, filed on Jun. 21, 2010, now U.S. Pat. No. 8,952,138; which claims the benefit of U.S. Provisional Application No. 61/219,257 filed Jun. 22, 2009, which is incorporated by reference herein.

FIELD OF THE INVENTION

The present invention generally relates to refolding proteins at high concentrations, and more particularly to refolding proteins in volumes at concentrations of 2.0 g/L and above.

BACKGROUND OF THE INVENTION

Recombinant proteins can be expressed in a variety of expression systems, including non-mammalian cells, such as bacteria and yeast. A difficulty associated with the expression of recombinant proteins in prokaryotic cells, such as bacteria, is the precipitation of the expressed proteins in limited-solubility intracellular precipitates typically referred to as inclusion bodies. Inclusion bodies are formed as a result of the inability of a bacterial host cell to fold recombinant proteins properly at high levels of expression and as a consequence the proteins become insoluble. This is particularly true of prokaryotic expression of large, complex or protein sequences of eukaryotic origin. Formation of incorrectly folded recombinant proteins has, to an extent, limited the commercial utility of bacterial fermentation to produce recombinant large, complex proteins, at high levels of efficiency.

Since the advent of the recombinant expression of proteins at commercially viable levels in non-mammalian expression systems such as bacteria, various methods have been developed for obtaining correctly folded proteins from bacterial inclusion bodies. These methods generally follow the procedure of expressing the protein, which typically precipitates in inclusion bodies, lysing the cells, collecting the inclusion bodies and then solubilizing the inclusion bodies in a solubilization buffer comprising a denaturant or surfactant and optionally a reductant, which unfolds the proteins and disassembles the inclusion bodies into individual protein chains with little to no structure. Subsequently, the protein chains are diluted into or washed with a refolding buffer that supports renaturation to a biologically active form. When cysteine residues are present in the primary amino acid sequence of the protein, it is often necessary to accomplish the refolding in an environment which allows correct formation of disulfide bonds (e.g., a redox system).

Typical refold concentrations for complex molecules, such as molecules comprising two or more disulfides, are less than 2.0 g/L and more typically 0.01-0.5 g/L (Rudolph & Lilie, (1996) FASEB J. 10:49-56). Thus, refolding large masses of a complex protein, such as an antibody, peptibody or other Fc fusion protein, at industrial production scales poses significant limitations due to the large volumes required to refold proteins, at these typical product concentration, and is a common problem facing the industry. One factor that limits the refold concentration of these types of proteins is the formation of incorrectly paired disulfide bonds, which may in turn increase the propensity for those forms of the protein to aggregate. Due to the large volumes of material and large pool sizes involved when working with industrial scale protein production, significant time, and resources can be saved by eliminating or simplifying one or more steps in the process.

While protein refolding has previously been demonstrated at higher concentrations, the proteins that were refolded were either significantly smaller in molecular weight, less complex molecules containing only one or two disulfide bonds (see, e.g., Creighton, (1974) J. Mol. Biol. 87:563-577). Additionally, the refolding processes for such proteins employed detergent-based refolding chemistries (see, e.g., Stockel et al., (1997) Eur J Biochem 248:684-691) or utilized high pressure folding strategies (St John et al., (2001) J. Biol. Chem. 276(50):46856-63). More complex molecules, such as antibodies, peptibodies and other large proteins, are generally not amenable to detergent refold conditions and are typically refolded in chaotropic refold solutions. These more complex molecules often have greater than two disulfide bonds, often between 8 and 24 disulfide bonds, and can be multi-chain proteins that form homo- or hetero-dimers.

Until the present disclosure, these types of complex molecules could not be refolded at high concentrations, i.e., concentrations of 2.0 g/L and higher, with any meaningful degree of efficiency on a small scale, and notably not on an industrial scale. The disclosed methods, in contrast, can be performed at high concentrations on a small or large (e.g, industrial) scale to provide properly refolded complex proteins. The ability to refold proteins at high concentrations and at large scales can translate into not only enhanced efficiency of the refold operation itself, but also represents time and cost savings by eliminating the need for additional equipment and personnel. Accordingly, a method of refolding proteins present in high concentrations could translate into higher efficiencies and cost savings to a protein production process.

BRIEF DESCRIPTION OF THE DRAWINGS

FIG. 1a depicts the effect of a 5 mM buffer strength; FIG. 1b depicts the effect of a 7.5 mM buffer strength; FIG. 1c depicts the effect of a 10 mM buffer strength; FIG. 1d depicts the effect of a 12.5 mM buffer strength; FIG. 1e depicts the effect of a 15 mM buffer strength; and FIG. 1f depicts the effect of a 20 mM buffer strength.

SUMMARY OF THE INVENTION

Figure 1A:
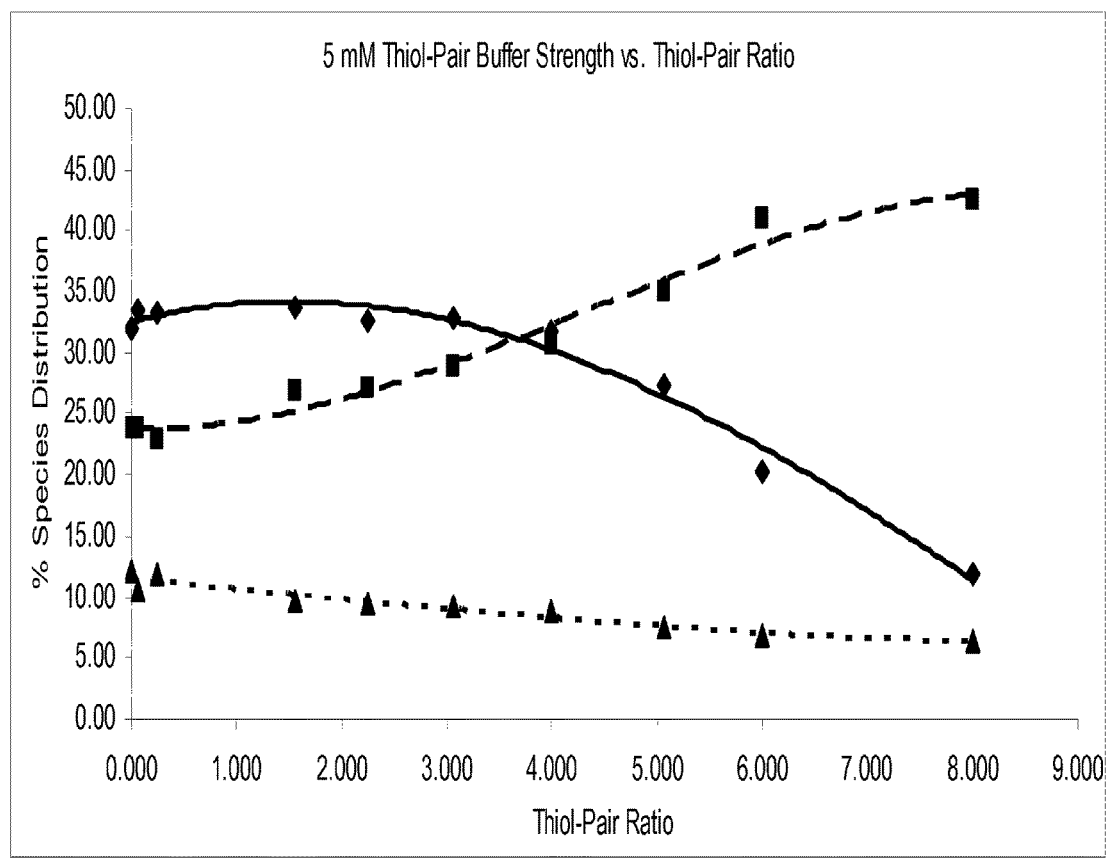
FIGS. 1a-1f are a series of plots depicting the effect of thiol-pair ratio and redox buffer strength on product-species distribution.
Figure 1B:
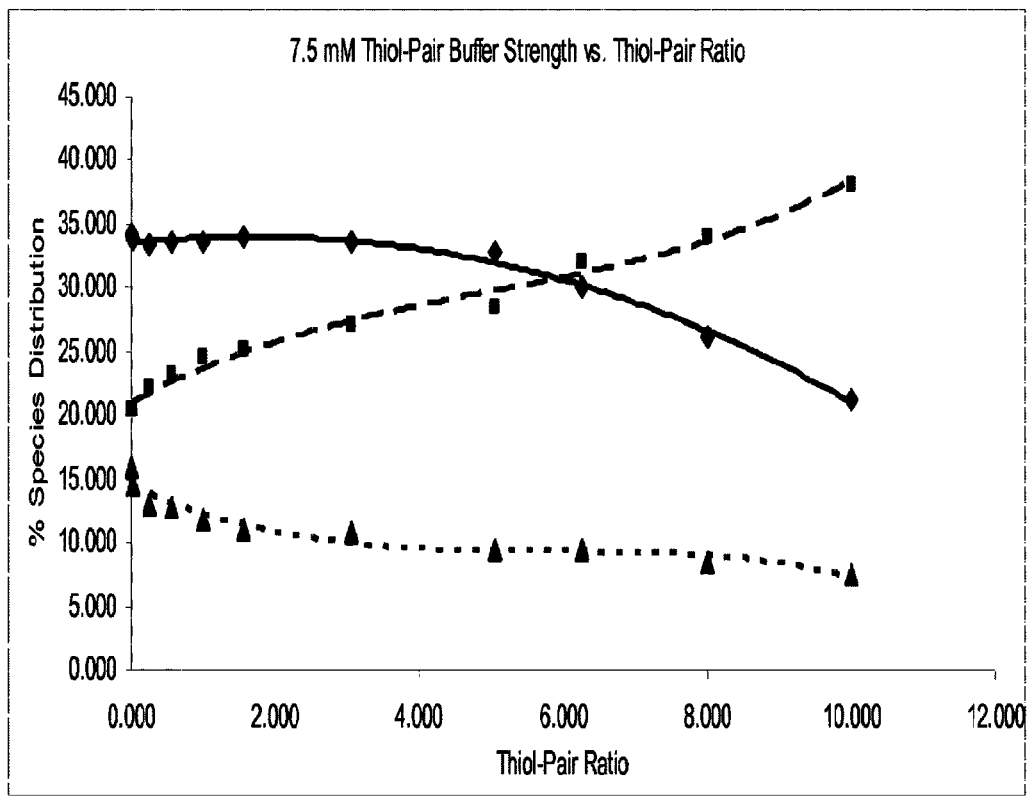
Figure 1C:
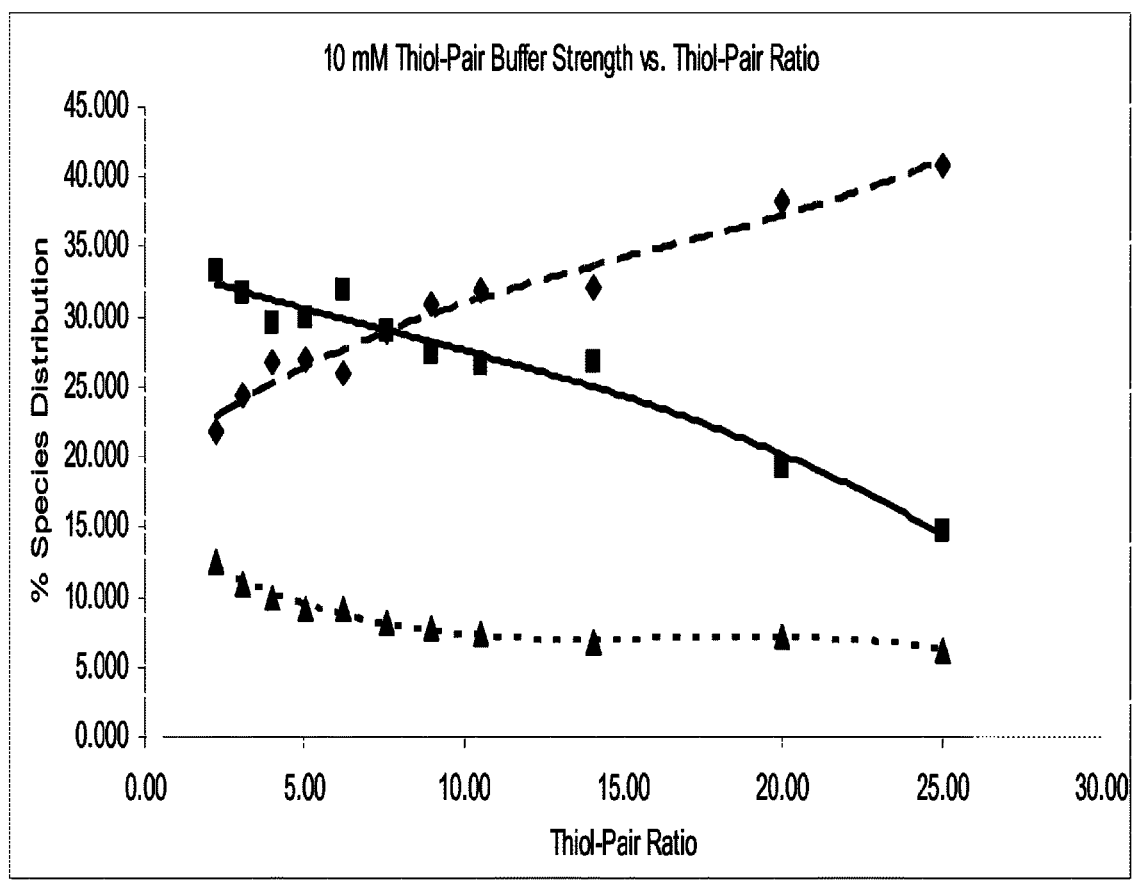
Figure 1D:
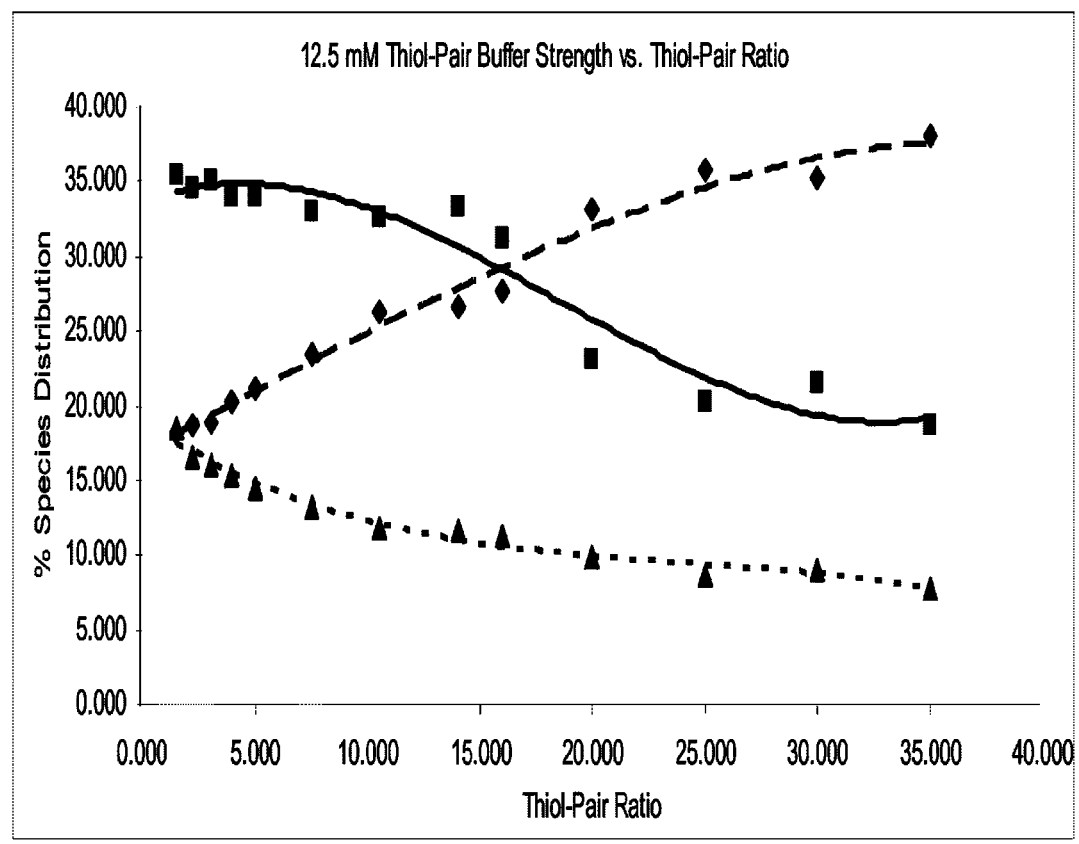
Figure 1E:
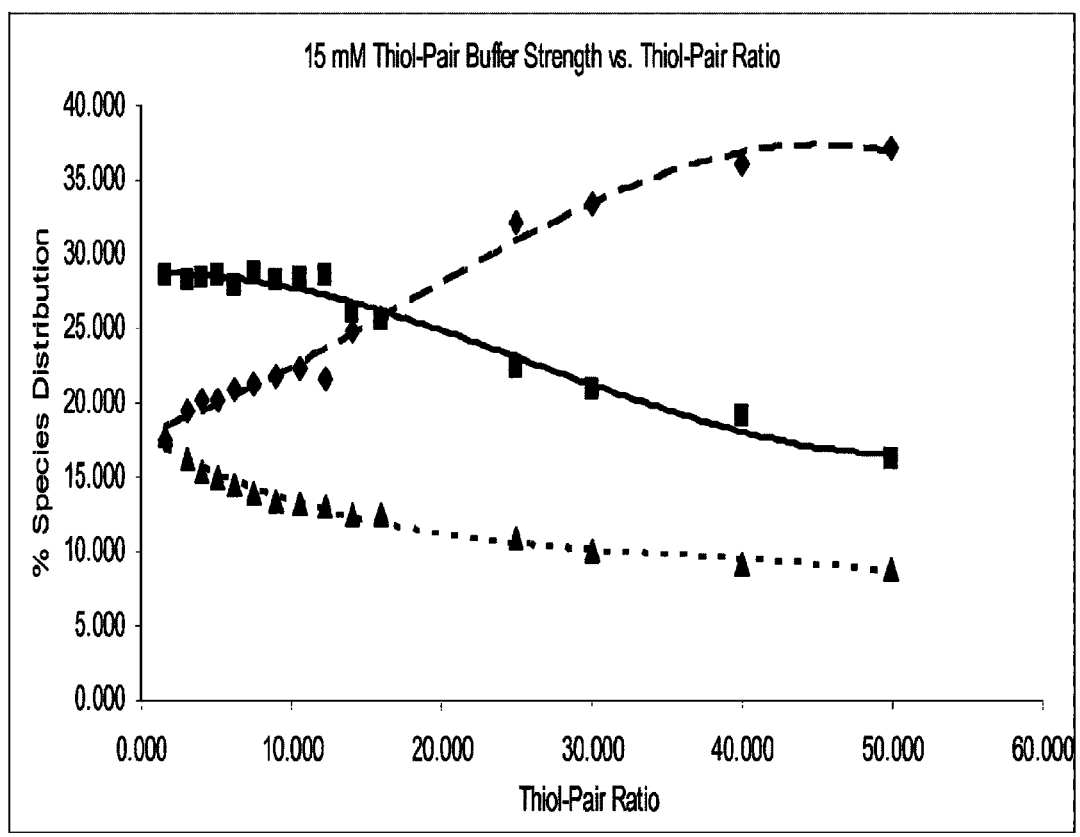
Figure 1F:
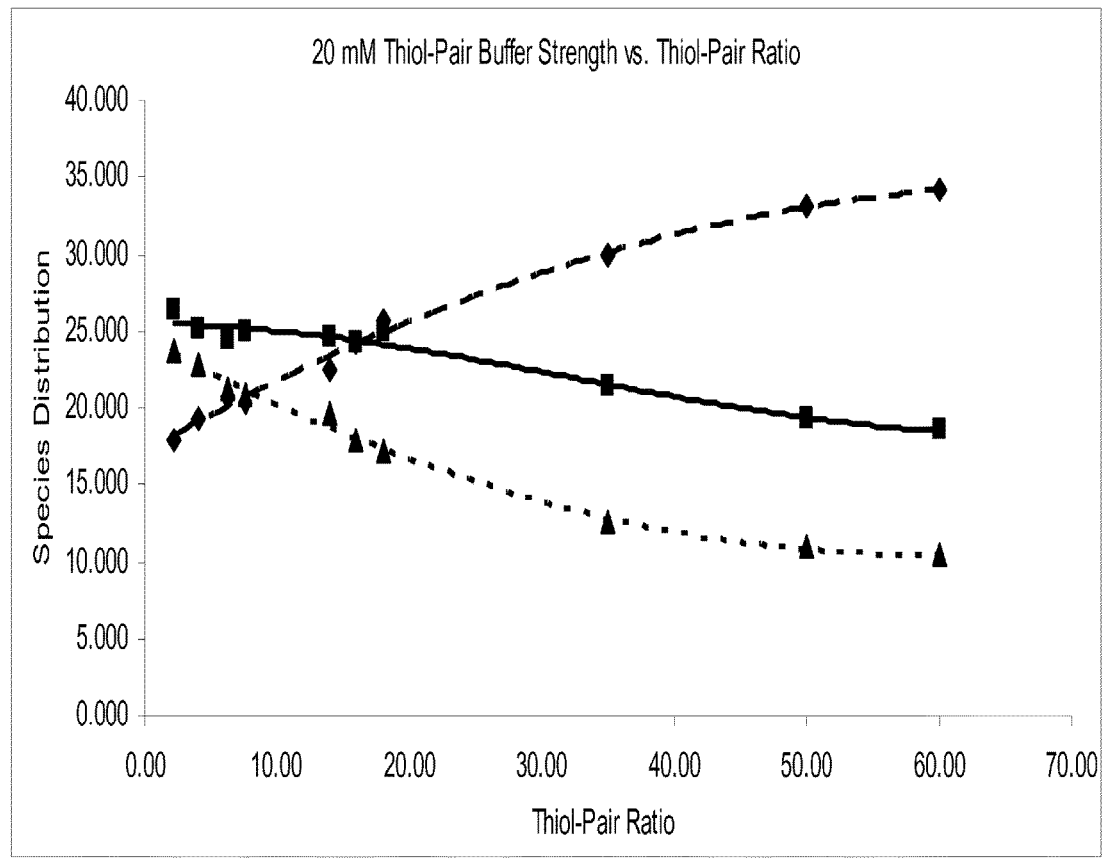

A method of refolding a protein expressed in a non-mammalian expression system and present in a volume at a concentration of 2.0 g/L or greater comprising: (a) contacting the protein with a refold buffer comprising a redox component comprising a final thiol-pair ratio having a range of 0.001 to 100 and a redox buffer strength of 2 mM or greater and one or more of: (i) a denaturant; (ii) an aggregation suppressor; and (iii) a protein stabilizer, to form a refold mixture; (b) incubating the refold mixture; and (c) isolating the protein from the refold mixture.

In various embodiments the redox component has a final thiol-pair ratio greater than or equal to 0.001 but less than or equal to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50 and a Thiol-pair buffer strength equal to or greater than 2 mM, for example greater than or equal to 2.25 mM, 2.5 mM, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength can be between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, to form a mixture.

In one embodiment of a refold buffer, the refold buffer comprises urea, arginine-HCl, cysteine and cystamine in Tris buffer. In a further embodiment the components are present in the refold buffer in proportions described in Example 3.

In another embodiment of a refold buffer, the refold buffer comprises urea, arginine HCl, glycerol, cysteine, and cystamine in Tris buffer. In a further embodiment the components are present in the refold buffer in proportions described in Example 4.

In some embodiments, the protein is initially present in a volume in a non-native limited solubility form, such as an inclusion body. Alternatively, the protein is present in the volume in a soluble form. The protein can be a recombinant protein or it can be an endogenous protein. The protein can be a complex protein such as an antibody or a multimeric protein. In another embodiment, the protein is an Fc-protein conjugate, such as a protein fused or linked to a Fc domain.

The non-mammalian expression system can be a bacterial expression system or a yeast expression system.

The denaturant in the refold buffer can be selected from the group consisting of urea, guanidinium salts, dimethyl urea, methylurea and ethylurea. The protein stabilizer in the refold buffer can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes. The aggregation suppressor can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes. The thiol-pairs can comprise at least one component selected from the group consisting of glutathione-reduced, glutathione-oxidized, cysteine, cystine, cysteamine, cystamine and beta-mercaptoethanol.

In various embodiments, the purification can comprise contacting the mixture with an affinity separation matrix, such as a Protein A or Protein G resin. Alternatively, the affinity resin can be a mixed mode separation matrix or an ion exchange separation matrix. In various aspects, the incubation can be performed under aerobic conditions or under non-aerobic conditions.

DETAILED DESCRIPTION OF THE INVENTION

The relevant literature suggests that when optimizing various protein refolding operations, the refold buffer thiol-pair ratio has been purposefully varied and as a result the thiol buffer strength was unknowingly varied across a wide range of strengths (see, e.g., Lilie, Schwarz & Rudolph, (1998) *Current Opinion in Biotechnology* 9(5):497-501, and Tran-Moseman, Schauer & Clark (1999) *Protein Expression & Purification* 16(1):181-189). In one study, a relationship between the thiol pair ratio and the buffer strength was investigated for lysozyme, a simple, single-chain protein that forms a molten globule. (De Bernardez et al., (1998) *Biotechnol. Prog.* 14:47-54). The De Bernardez work described thiol concentration in terms of a model that considered only the kinetics of a one-way reaction model. However, most complex proteins are governed by reversible thermodynamic equilibria that are not as easily described (see, e.g., Darby et al., (1995) *J. Mol. Biol.* 249:463-477). More complex behavior is expected in the case of large multi-chain proteins containing many disulfide bonds, such as antibodies, peptibodies and other Fc fusion proteins. Until the present disclosure, specific relationships had not been provided for thiol buffer strength, thiol-pair ratio chemistry, and protein concentration with respect to complex proteins that related to the efficiency of protein production. Consequently, the ability to refold proteins in a highly concentrated volume has largely been an inefficient or unachievable goal, leading to bottlenecks in protein production, particularly on the industrial scale.

Prior to the present disclosure a specific controlled investigation of the independent effects of thiol-pair ratio and thiol-pair buffer strength had not been disclosed for complex proteins. As described herein, by controlling the thiol-pair buffer strength, in conjunction with thiol-pair ratio and protein concentration, the efficiency of protein folding operations can be optimized and enhanced and the refolding of proteins at high concentrations, for example 2 g/L or greater, can be achieved.

Thus, in one aspect, the present disclosure relates to the identification and control of redox thiol-pair ratio chemistries that facilitate protein refolding at high protein concentrations, such as concentrations higher than 2.0 g/L. The method can be applied to any type of protein, including simple proteins and complex proteins (e.g., proteins comprising 2-23 disulfide bonds or greater than 250 amino acid residues, or having a MW of greater than 20,000 daltons), including proteins comprising a Fc domain, such as antibodies, peptibodies and other Fc fusion proteins, and can be performed on a laboratory scale (typically milliliter or liter scale), a pilot plant scale (typically hundreds of liters) or an industrial scale (typically thousands of liters). Examples of complex molecules known as peptibodies, and other Fc fusions, are described in U.S. Pat. No. 6,660,843, U.S. Pat. No. 7,138,370 and U.S. Pat. No. 7,511,012.

As described herein, the relationship between thiol buffer strength and redox thiol-pair ratio has been investigated and optimized in order to provide a reproducible method of refolding proteins at concentrations of 2.0 g/L and higher on a variety of scales. A mathematical formula was deduced to allow the precise calculation of the ratios and strengths of individual redox couple components to achieve matrices of buffer thiol-pair ratio and buffer thiol strength. Once this relationship was established, it was possible to systematically demonstrate that thiol buffer strength and the thiol-pair ratio interact to define the distribution of resulting product-related species in a refolding reaction.

The buffer thiol-pair ratio is, however, only one component in determining the total system thiol-pair ratio in the total reaction. Since the cysteine residues in the unfolded protein are reactants as well, the buffer thiol strength needs to vary in proportion with increases in protein concentration to achieve the optimal system thiol-pair ratio. Thus, in addition to demonstrating that buffer thiol strength interacts with the thiol-pair ratio, it has also been shown that the buffer thiol strength relates to the protein concentration in the total reaction as well. Optimization of the buffer thiol strength and the system thiol pair ratio can be tailored to a particular protein, such as a complex protein, to minimize cysteine mispairing yet still facilitate a refold at a high concentration.

I. Definitions

As used herein, the terms "a" and "an" mean one or more unless specifically indicated otherwise.

As used herein, the term "non-mammalian expression system" means a system for expressing proteins in cells derived from an organism other than a mammal, including but not limited to, prokaryotes, including bacteria such as $E.$ $coli$, and yeast. Often a non-mammalian expression system is employed to express a recombinant protein of interest, while in other instances a protein of interest is an endogenous protein that is expressed by a non-mammalian cell. For purposes of the present disclosure, regardless of whether a protein of interest is endogenous or recombinant, if the protein is expressed in a non-mammalian cell then that cell is a "non-mammalian expression system." Similarly, a "non-mammalian cell" is a cell derived from an organism other than a mammal, examples of which include bacteria or yeast.

As used herein, the term "denaturant" means any compound having the ability to remove some or all of a protein's secondary and tertiary structure when placed in contact with the protein. The term denaturant refers to particular chemical compounds that affect denaturation, as well as solutions comprising a particular compound that affect denaturation. Examples of denaturants that can be employed in the disclosed method include, but are not limited to urea, guanidinium salts, dimethyl urea, methylurea, ethylurea and combinations thereof.

As used herein, the term "aggregation suppressor" means any compound having the ability to disrupt and decrease or eliminate interactions between two or more proteins. Examples of aggregation suppressors can include, but are not limited to, amino acids such as arginine, proline, and glycine; polyols and sugars such as glycerol, sorbitol, sucrose, and trehalose; surfactants such as, polysorbate-20, CHAPS, Triton X-100, and dodecyl maltoside; and combinations thereof.

As used herein, the term "protein stabilizer" means any compound having the ability to change a protein's reaction equilibrium state, such that the native state of the protein is improved or favored. Examples of protein stabilizers can include, but are not limited to, sugars and polyhedric alcohols such as glycerol or sorbitol; polymers such as polyethylene glycol (PEG) and α-cyclodextrin; amino acids salts such as arginine, proline, and glycine; osmolytes and certain Hoffmeister salts such as Tris, sodium sulfate and potassium sulfate; and combinations thereof.

As used herein, the terms "Fc" and "Fe region" are used interchangeably and mean a fragment of an antibody that comprises human or non-human (e.g., murine) $C_{H2}$ and $C_{H3}$ immunoglobulin domains, or which comprises two contiguous regions which are at least 90% identical to human or non-human $C_{H2}$ and $C_{H3}$ immunoglobulin domains. An Fc can but need not have the ability to interact with an Fc receptor. See, e.g., Hasemann & Capra, "Immunoglobulins: Structure and Function," in William E. Paul, ed., $Fundamental$ $Immunology$, Second Edition, 209, 210-218 (1989), which is incorporated by reference herein in its entirety.

As used herein, the terms "protein" and "polypeptide" are used interchangeably and mean any chain of at least five naturally or non-naturally occurring amino acids linked by peptide bonds.

As used herein, the terms "isolated" and "purify" are used interchangeably and mean to reduce by 1%, 2%, 3%, 4%, 5%, 10%, 15%, 20%, 25%, 30%, 35%, 40%, 45%, 50%, 55%, 60%, 65%, 70%, 75%, 80%, 85%, 90% or 95%, or more, the amount of heterogenous elements, for example biological macromolecules such as proteins or DNA, that may be present in a sample comprising a protein of interest. The presence of heterogenous proteins can be assayed by any appropriate method including High-performance Liquid Chromatography (HPLC), gel electrophoresis and staining and/or ELISA assay. The presence of DNA and other nucleic acids can be assayed by any appropriate method including gel electrophoresis and staining and/or assays employing polymerase chain reaction.

As used herein, the term "complex molecule" means any protein that is (a) larger than 20,000 MW, or comprises greater than 250 amino acid residues, and (b) comprises two or more disulfide bonds in its native form. A complex molecule can, but need not, form multimers. Examples of complex molecules include but are not limited to, antibodies, peptibodies and other chimeric molecules comprising an Fc domain and other large proteins. Examples of complex molecules known as peptibodies, and other Fc fusions, are described in U.S. Pat. No. 6,660,843, U.S. Pat. No. 7,138,370 and U.S. Pat. No. 7,511,012.

As used herein, the term "peptibody" refers to a polypeptide comprising one or more bioactive peptides joined together, optionally via linkers, with an Fc domain. See U.S. Pat. No. 6,660,843, U.S. Pat. No. 7,138,370 and U.S. Pat. No. 7,511,012 for examples of peptibodies.

As used herein, the term "refolding" means a process of reintroducing secondary and tertiary structure to a protein that has had some or all of its native secondary or tertiary structure removed, either in vitro or in vivo, e.g., as a result of expression conditions or intentional denaturation and/or reduction. Thus, a refolded protein is a protein that has had some or all of its native secondary or tertiary structure reintroduced.

As used herein, the term "buffer thiol-pair ratio" is defined by the relationship of the reduced and oxidized redox species used in the refold buffer as defined in Equation 1:

Definition of Buffer Thiol-Pair Ratio ($TPR$)      Equation 1

$$\text{Buffer } TPR = \frac{[\text{reductant}]^2}{[\text{oxidant}]} = \frac{[\text{cysteine}]^2}{[\text{cystamine}]}.$$

As used herein, the terms "Buffer Thiol Strength", "Thiol-Pair Buffer Strength", and "Thiol-pair Strength" are used interchangeably and are defined in Equation 2, namely as the total mono-equivalent thiol concentration, wherein the total concentration is the sum of the reduced species and twice the concentration of the oxidized species.

Definition of Buffer Thiol-Pair Buffer Strength/Thiol Buffer Strength (BS)

Thiol-Pair Buffer Strength=2[oxidant]+[reductant]=2 [cystamine]+[cysteine]      Equation 2.

The relationship between the thiol-pair ratio and thiol-pair buffer strength is described in equations 3 and 4.

Calculation of the Reduced Redox Species with Regard to a Defined Redox Buffer Strength ($BS$) and buffer Redox Potential    Equation 3

Concentration of Reduced Redox Component =

$$\frac{\left(\sqrt{bufferTPR^2 + 8*bufferTPR*BS}\right) - bufferTPR}{4}.$$

Calculation of the Oxidized Redox Species with Regard to a Defined Redox Buffer Strength ($BS$) and Buffer Redox Potential    Equation 4

Concentration of Oxidized Redox Component =

$$\frac{(\text{Concentration of Reduced Redox Component})^2}{TPR}.$$

As used herein, the term "redox component" means any thiol-reactive chemical or solution comprising such a chemical that facilitates a reversible thiol exchange with another thiol or the cysteine residues of a protein. Examples of such compounds include, but are not limited to, glutathione-reduced, glutathione-oxidized, cysteine, cystine, cysteamine, cystamine, beta-mercaptoethanol and combinations thereof.

As used herein, the term "solubilization" means a process in which salts, ions, denaturants, detergents, reductants and/or other organic molecules are added to a solution comprising a protein of interest, thereby removing some or all of a protein's secondary and/or tertiary structure and dissolving the protein into the solvent. This process can include the use of elevated temperatures, typically 10-50° C., but more typically 15-25° C., and/or alkaline pH, such as pH 7-12. Solubilization can also be accomplished by the addition of acids, such as 70% formic acid (see, e.g., Cowley & Mackin (1997) *FEBS Lett* 402:124-130).

A "solubilized protein" is a protein in which some or all of the protein's secondary and/or tertiary structure has been removed.

A "solublization pool" is a volume of solution comprising a solubilized protein of interest as well as the salts, ions, denaturants, detergents, reductants and/or other organic molecules selected to solubilize the protein.

As used herein, the term "non-aerobic condition" means any reaction or incubation condition that is performed without the intentional aeration of the mixture by mechanical or chemical means. Under non-aerobic conditions oxygen can be present, as long as it is naturally present and was not introduced into the system with the intention of adding oxygen to the system. Non-aerobic conditions can be achieved by, for example, limiting oxygen transfer to a reaction solution by limiting headspace pressure, the absence of, or limited exposure to, air or oxygen contained in the holding vessel, air or oxygen overlay, the lack of special accommodations to account for mass transfer during process scaling, or the absence of gas sparging or mixing to encourage the presence of oxygen in the reaction system. Non-aerobic conditions can also be achieved by intentionally limiting or removing oxygen from the system via chemical treatment, headspace overlays or pressurization with inert gases or vacuums, or by sparging with gases such as argon or nitrogen, results in the reduction of oxygen concentration in the reaction mixture.

As used herein, the terms "non-native" and "non-native form" are used interchangeably and when used in the context of a protein of interest, such as a protein comprising a Fc domain, mean that the protein lacks at least one formed structure attribute found in a form of the protein that is biologically active in an appropriate in vivo or in vitro assay designed to assess the protein's biological activity. Examples of structural features that can be lacking in a non-native form of a protein can include, but are not limited to, a disulfide bond, quaternary structure, disrupted secondary or tertiary structure or a state that makes the protein biologically inactive in an appropriate assay. A protein in a non-native form can but need not form aggregates.

As used herein, the term "non-native limited solubility form" when used in the context of a protein of interest, such as a protein comprising a Fc domain, means any form or state in which the protein lacks at least one formed structural feature found in a form of the protein that (a) is biologically active in an appropriate in vivo or in vitro assay designed to assess the protein's biological activity and/or (b) forms aggregates that require treatment, such as chemical treatment, to become soluble. The term specifically includes proteins existing in inclusion bodies, such as those sometimes found when a recombinant protein is expressed in a non-mammalian expression system.

II. Theory

Refolding microbial-derived molecules present in a pool at concentrations of 2.0 g/L or higher is advantageous for a variety of reasons, primarily because of the associated reduction in reaction volumes and increases in process throughput. From a process scaling standpoint, it is advantageous to refold under conditions that do not require aerobic conditions; such conditions can be achieved, for example, by constant or intermittent sparging, the implementation of air or oxygen headspace overlays, by pressurizing the headspace, or by employing high efficiency mixing. Since the oxygen concentration in the system is related to mass transfer, the scaling of the refold reaction becomes considerably more difficult as factors such as tank geometry, volume, and mixing change. Furthermore, oxygen may not be a direct reactant in the formation of disulfide bonds in the protein, making a direct link to the mass transfer coefficient unlikely. This further complicates scaling of the reaction. Therefore, non-aerobic, chemically controlled redox systems are preferred for refolding proteins. Examples of such conditions are provided herein.

The optimal refold chemistry for a given protein represents a careful balance that maximizes the folded/oxidized state while minimizing undesirable product species, such as aggregates, unformed disulfide bridges (e.g., reduced cysteine pairs), incorrect disulfide pairings (which can lead to misfolds), oxidized amino acid residues, deamidated amino acid residues, incorrect secondary structure, and product-related adducts (e.g., cysteine or cysteamine adducts). One factor that is important in achieving this balance is the redox-state of the refold system. The redox-state is affected by many factors, including, but not limited to, the number of cysteine residues contained in the protein, the ratio and concentration of the redox couple chemicals in the refold solution (e.g., cysteine, cystine, cystamine, cysteamine, glutathione-reduced and glutathione-oxidized), the concentration of reductant carried over from the solubilization buffer (e.g., DTT, glutathione and beta-mercaptoethanol), the level of heavy metals in the mixture, and the concentration of oxygen in the solution.

Thiol-pair ratio and thiol-pair buffer strength are defined in Equations 1 and 2, infra, using cysteine and cystamine as an example reductant and oxidant, respectively. These quantities, coupled with protein concentration and reductant carry-over from the solubilization, can be factors in achieving a balance between the thiol-pair ratio and the thiol-pair buffer strength.

Turning to FIGS. 1a-1f, these figures depict the effect of thiol-pair ratio and thiol buffer strength on the distribution of product-related species, as visualized by reversed phase-HPLC analysis, for a complex dimeric protein. In FIGS. 1a-1f, the dotted lines represent protein species with oxidized amino acid residues, single chain species, and stable mixed disulfide intermediates, the dashed lines represent mis-paired or incorrectly formed disulfide protein species and protein species with partially unformed disulfide linkages. The solid lines represent properly folded protein species. FIGS. 1a-1f demonstrate that at a constant 6 g/L protein concentration, as the thiol-pair buffer strength is increased, the thiol-pair ratio required to achieve a comparable species distribution must also increase. For example, as shown in FIGS. 1a-1f, if the buffer strength is increased to 10 mM, from 5 mM, the balanced thiol-pair ratio would be about 2-fold higher, to achieve a comparable species distribution. This is largely due to increased buffering of the reductant carried over from the solubilization, on the total system thiol-pair ratio. At lower redox buffer strengths, the overall system becomes much more difficult to control. The protein concentration and number of cysteines contained in the protein sequence also relate to the minimum required thiol-pair buffer strength required to control the system. Below a certain point, which will vary from protein to protein, the protein thiol concentration can overwhelm the redox couple chemistry and lead to irreproducible results.

In the results depicted in FIGS. 1a-1f, when the thiol-pair ratio of the refolding solution is intentionally set to be more reducing, the resultant product distribution shifts to produce more of the reduced product species (dashed lines). When the Thiol-Pair Ratio of the refolding solution is intentionally set to be lower, or more oxidizing, the resultant product distribution shifts to produce more oxidized residues, single chain forms, and stable mixed disulfide intermediate species (dotted lines). The ability to select an optimal Thiol-Pair Ratio and Thiol-pair Buffer Strength allows for the optimization of the yield of a desired folded protein form. This optimized yield can be achieved by maximizing the mass or yield of desired folded protein species in the refolding pool or by purposefully shifting the resultant undesired product-related species to a form that is most readily removed in the subsequent purification steps and thusly leads to an overall benefit to process yield or purity.

Optimization of the redox component Thiol-pair Ratios and Thiol-pair Buffer Strengths can be performed for each protein. A matrix or series of multifactorial matrices can be evaluated to optimize the refolding reaction for conditions that optimize yield and distributions of desired species. An optimization screen can be set up to systematically evaluate redox chemistries, Thiol-pair ratios, Thiol-pair Buffer Strengths, incubation times, protein concentration and pH in a full or partial factorial matrix, with each component varied over a range of at least three concentration or pH levels with all other parameters kept constant. The completed reactions can be evaluated by RP-HPLC and SE-HPLC analysis for yield and product quality using standard multivariate statistical tools.

III. Method of Refolding a Protein Expressed in a Non-Mammalian Expression System and Present in a Volume at a Concentration of 2.0 g/L or Greater The disclosed refold method is particularly useful for refolding proteins expressed in non-mammalian expression systems. As noted herein, non-mammalian cells can be engineered to produce recombinant proteins that are expressed intracellularly in either a soluble or a completely insoluble or non-native limited solubility form. Often the cells will deposit the recombinant proteins into large insoluble or limited solubility aggregates called inclusion bodies. However, certain cell growth conditions (e.g., temperature or pH) can be modified to drive the cells to produce a recombinant protein in the form of intracellular, soluble monomers. As an alternative to producing proteins in insoluble inclusion bodies, proteins can be expressed as soluble proteins, including proteins comprising an Fc region, which can be captured directly from cell lysate by affinity chromatography. Capturing directly from lysate allows for the refolding of relatively pure protein and avoids the very intensive harvesting and separation process that is required in inclusion body processes. The refolding method, however, is not limited to samples that have been affinity purified and can be applied to any sample comprising a protein that was expressed in a non-mammalian expression system, such as a protein found in a volume of cell lysate (i.e., a protein that has not been purified in any way).

In one aspect, the present disclosure relates to a method of refolding a protein expressed in a non-mammalian expression system in a soluble form and present in a volume at a concentration of 2.0 g/L or greater, such as a protein that has been purified by affinity chromatography from the cell lysate of non-mammalian cells in which the protein was expressed. Although the volume can be derived from any stage of a protein purification process, in one example the volume is an affinity chromatography elution pool (e.g., a Protein A elution pool). In another example, the volume is situated in a process stream. The method is not confined to Fc-containing proteins, however, and can be applied to any kind of peptide or protein that is expressed in a soluble form and captured from non-mammalian-derived cell lysate. The isolated soluble protein is often released from non-mammalian cells in a reduced form and therefore can be prepared for refolding by addition of a denaturant, such as a chaotrope. Further combination with protein stabilizers, aggregation suppressors and redox components, at an optimized Thiol-pair ration and Thiol-pair Buffer Strength, allows for refolding at concentrations of 1-40 g/L, for example at concentrations of 10-20 g/L.

In one particular embodiment of the method, a protein is expressed in a non-mammalian expression system, and is released from the expressing cell by high pressure lysis. The protein is then captured from the lysate by Protein A affinity chromatography and is present in a volume at a concentration of 10 g/L or greater. The protein is then contacted with a refold buffer comprising a denaturant, an aggregation suppressor, a protein stabilizer and a redox component, wherein the redox component has a final thiol-pair ratio (as defined herein) having a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50 and a Thiol-pair buffer strength (as defined herein) equal to or greater than 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM.

In another aspect, the present disclosure relates to a method of refolding a protein expressed in a non-mammalian expression system in an insoluble or limited-solubility form, such as in the form of inclusion bodies. When the protein is disposed in inclusion bodies, the inclusion bodies can be harvested from lysed cells, washed, concentrated and refolded.

Optimization of the refold buffer can be performed for each protein and each final protein concentration level using the novel method provided herein. As shown in the Examples, good results can be obtained when refolding a protein comprising an Fc region when the refold buffer contains a denaturant (e.g., urea or other chaotrope, organic solvent or strong detergent), aggregation suppressors (e.g., a mild detergent, arginine or low concentrations of PEG), protein stabilizers (e.g., glycerol, sucrose or other osmolyte, salts) and redox components (e.g., cysteine, cystamine, glutathione). The optimal thiol-pair ratio and redox buffer strength can be determined using an experimental matrix of thiol-pair ratio (which can have a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50) versus thiol-pair buffer strength (which can be greater than 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, depending on the protein concentration and the concentration of reductant used to solubilize the inclusion bodies). Conditions can be optimized using the novel methods described in Example 2.

In one particular embodiment of the method, a protein is expressed in a non-mammalian expression system and is present in a volume at a concentration of 2.0 g/L or greater. The protein is contacted with a refold buffer comprising a denaturant, an aggregation suppressor, a protein stabilizer and a redox component, wherein the redox component has a final thiol-pair ratio (as defined herein) having a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50, and a Thiol-pair buffer strength (as defined herein) equal to or greater than 2 mM, for example greater than or equal to 2.25 mM, 2.5 mM, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM, to form a mixture. A wide range of denaturant types may be employed in the refold buffer. Examples of some common denaturants that can be employed in the refold buffer include urea, guanidinium, dimethyl urea, methylurea, or ethylurea. The specific concentration of the denaturant can be determined by routine optimization, as described herein.

A wide range of protein stabilizers or aggregation suppressors can be employed in the refold buffer. Examples of some common aggregation suppressors that can be useful in the refold buffer include arginine, proline, polyethylene glycols, non-ionic surfactants, ionic surfactants, polyhydric alcohols, glycerol, sucrose, sorbitol, glucose, Tris, sodium sulfate, potassium sulfate, other osmolytes, or similar compounds. The specific concentration of the aggregation suppressor can be determined by routine optimization, as described herein.

A redox component of the refold buffer can be of any composition, with the caveat that the redox component has a final thiol-pair ratio in a range of 0.001 to 100, for example within a range of 0.05 to 50, 0.1 to 50, 0.25 to 50, 0.5 to 50, 0.75 to 40, 1.0 to 50 or 1.5 to 50, 2 to 50, 5 to 50, 10 to 50, 15 to 50, 20 to 50, 30 to 50 or 40 to 50, and a Thiol-pair buffer strength of greater than or equal to 2 mM, for example greater than or equal to 2.25 mM, 2.5, 2.75 mM, 3 mM, 5 mM, 7.5 mM, 10 mM, or 15 mM, wherein the thiol-pair buffer strength is effectively bounded at a maximum of 100 mM. Restated, in terms of ranges, the thiol buffer strength is between 2 and 20 mM, for example between 2.25 mM and 20 mM, 2.5 mM and 20 mM, 2.75 mM and 20 mM, 3 mM and 20 mM, 5 mM and 20 mM, 7.5 mM and 20 mM, 10 mM and 20 mM, or 15 mM and 20 mM. Methods of identifying a suitable redox component, i.e., determining appropriate thiol-pair ratios and redox buffer strengths, are known and/or are provided herein. Examples of specific thiol pairs that can form the redox component can include one or more of reduced glutathione, oxidized glutathione, cysteine, cystine, cysteamine, cystamine, and beta-mercaptoethanol. Thus, a thiol-pair can comprise, for example, reduced glutathione and oxidized glutathione. Another example of a thiol pair is cysteine and cystamine. The redox component can be optimized as described herein.

After the protein has been contacted with a redox component having the recited thiol pair ratio and redox buffer strength to form a refold mixture, the refold mixture is then incubated for a desired period of time. The incubation can be performed under non-aerobic conditions, as defined herein. Non-aerobic conditions need not be completely free of oxygen, only that no additional oxygen other than that present in the initial system is purposefully introduced. The incubation period is variable and is selected such that a stable refold mixture can be achieved with the desired analytical properties. An incubation period can be, for example, 1 hour, 4 hours, 12 hours, 24 hours, 48 hours, 72 hours, or longer.

Due to the sensitivity of high concentration refolds to the level of oxygen present in the system and the tendency for oxygen mass transfer to be greater at small-scale, a methodology and/or apparatus can be developed to control the oxygen levels and maintain non-aerobic conditions for the incubation step. In one embodiment, the procedure can comprise the preparation, dispensing and mixing of all refold components under a blanket of inert gas, such as nitrogen or argon, to avoid entraining levels of oxygen into the reaction. This approach is particularly helpful in identifying an acceptable thiol-pair ratio. In another embodiment useful at scales of 15 liters or less, the headspace of the refold reactor containing the protein and refold buffer can be purged with an inert gas or a mixture of inert gas and air or oxygen, and the reaction vessel sealed and mixed at a low rotational speed for the duration of the incubation time.

Following the incubation, the protein is isolated from the refold mixture. The isolation can be achieved using any known protein purification method. If the protein comprises a Fc domain, for example, a Protein A column provides an appropriate method of separation of the protein from the refold excipients. In other embodiments, various column chromatography strategies can be employed and will depend on the nature of the protein being isolated. Examples include HIC, AEX, CEX and SEC chromatography. Non-chromatographic separations can also be considered, such as precipitation with a salt, acid or with a polymer such as PEG (see, e.g., US 20080214795). Another alternative method for isolating the protein from the refold components can include dialysis or diafiltration with a tangential-flow filtration system.

In another exemplary refolding operation, inclusion bodies obtained from a non-mammalian expression system are solubilized in the range of 10 to 100 grams of protein per liter and more typically from 20-40 g/L for approximately 10-300 min. The solubilized inclusion bodies are then diluted to achieve reduction of the denaturants and reductants in the solution to a level that allows the protein to refold. The dilution results in protein concentration in the range of 1 to 15 g/L in a refold buffer containing urea, glycerol or sucrose, arginine, and the redox pair (e.g., cysteine and cystamine). In one embodiment the final composition is 1-4 M urea, 5-40% glycerol or sucrose, 25-500 mM arginine, 0.1-10 mM cysteine and 0.1-10 mM cystamine. The solution is then mixed during incubation over a time that can span from 1 hour to 4 days.

As noted herein, the disclosed method is particularly useful for proteins expressed in bacterial expression systems, and more particularly in bacterial systems in which the protein is expressed in the form of inclusion bodies within the bacterial cell. The protein can be a complex protein, i.e., a protein that (a) is larger than 20,000 MW, or comprises greater than 250 amino acid residues, and (b) comprises two or more disulfide bonds in its native form. When the protein is expressed in an inclusion body it is likely that any disulfide bond found in the protein's native form will be misformed or not formed at all. The disclosed method is applicable to these and other forms of a protein of interest. Specific examples of proteins that can be considered for refolding using the disclosed methods include antibodies, which are traditionally very difficult to refold at high concentrations using typical refold methods due to their relatively large size and number of disulfide bonds. The method can also be employed to refold other Fc-containing molecules such as peptibodies, and more generally to refold any fusion protein comprising an Fc domain fused to another protein.

Another aspect of the disclosed method is its scalability, which allows the method to be practiced on any scale, from bench scale to industrial or commercial scale. Indeed, the disclosed method will find particular application at the commercial scale, where it can be employed to efficiently refold large quantities of protein.

The present disclosure will now be illustrated by reference to the following examples, which set forth certain embodiments. However, it should be noted that these embodiments are illustrative and are not to be construed as restricting the invention in any way.

EXAMPLES

The Examples presented herein demonstrate that thiol-pair ratio and redox buffer strength is a significant consideration in achieving an efficient refolding reaction that is insensitive to environmental influences and aeration. This insensitivity is a consideration for the ease of scaling and on an industrial or commercial scale, the transfer of the process from plant to plant.

The Examples also demonstrate that at typical refolding reaction concentrations (0.01-2.0 g/L); the sensitivity to external aeration is relatively muted. However, at concentrations of about 2 g/L and above, the sensitivity of the refold reaction to the thiol-pair ratio and redox buffer strength is increased and nearly all of the chemical components, especially the redox components, may need to be adjusted to accommodate for changes in the protein concentration in the reaction.

Example 1

Expression of Recombinant Protein

In one experiment, recombinant proteins comprising an Fc moiety were expressed in a non-mammalian expression system, namely E. coli, and driven to form cytoplasmic deposits in the form of inclusion bodies. For each protein refolded the following procedure was followed.

After the completion of the expression phase, the cell broth was centrifuged and the liquid fraction removed, leaving the cells as a paste. The cells were resuspended in water to approximately 60% of the original volume. The cells were then lysed by means of three passes through a high pressure homogenizer. After the cells were lysed, the lysate was centrifuged in a disc-stack centrifuge to collect the protein in the solid fraction, which was expressed in a limited solubility non-native form, namely as inclusion bodies. The protein slurry was washed multiple times by repeatedly resuspending the captured solids slurry in water to between 50% and 80% of the original fermentation broth volume, mixing, and centrifugation to collect the protein in the solid fraction. The final washed inclusion bodies were captured and stored frozen.

Example 2

Identification of Refold Conditions/Redox Components

Multiple complex, microbial-derived proteins were evaluated. Each protein was solubilized in an appropriate level of guanidine and/or urea, typically at levels the equivalent of 4-6 M guanidine or 4-9 M urea, or combinations of both denaturants, which fully denatured the protein. The protein was reduced with DTT, 5-20 mM, at pH 8.5, and incubated at room temperature for approximately 1 hour.

Identification of the refold buffer was performed for each protein. A multifactorial matrix or a series of multifactorial matrices were evaluated to identify the refolding reaction for conditions that optimize yield and minimize aggregate formation. An identification screen was set up to systematically evaluate urea, arginine, glycerol and pH in a full factorial matrix, with each component varied over a range of at least three concentration or pH levels with all other parameters kept constant. The completed reactions were evaluated by RP-HPLC and SE-HPLC analysis for yield and product quality using standard multivariate statistical tools. A subset of the conditions having the desired behavior was then further evaluated in subsequent screens that evaluated a range of pH, thiol-pair ratio, thiol-pair buffer strength, and potentially further excipient levels in a factorial screen. Secondary interactions were also evaluated using standard multivariate statistical tools.

Best results, as determined by reversed-phase and size exclusion HPLC analysis, were observed using a refold buffer containing a denaturant (e.g., urea, dimethyl urea or other chaotrope at non-denaturing levels at levels between 1 and 4 M), an aggregation suppressor (e.g., arginine at levels between 5 and 500 mM), a protein stabilizer (e.g., glycerol or sucrose at levels between 5 and 40% w/v) and a redox component (e.g., cysteine or cystamine). The thiol-pair ratio and redox buffer strength were determined using an experimental matrix of thiol-pair ratio (0.1 to 100, more typically 1 to 25) versus buffer strength (typically 2 mM to 20 mM, depending on the protein concentration, the number of cysteine residues in the protein, and the concentration of reductant used to solubilize the inclusion bodies).

Individual reactions were formed with varying levels of cysteine and cystamine that would allow for a controlled matrix of thiol-pair ratio at various thiol-pair buffer strengths. The relationships were calculated using Equations 3 and 4. Each condition was screened under both aerobic and non-aerobic conditions, utilizing the techniques described herein. Optimum conditions were selected to meet a stable balance of yield, desired distribution of folding species, insensitivity to environmental oxidants (e.g., air), and insensitivity to normal variation in DTT carry-over from the solubilization step.

Example 3

High Concentration Refolding of Non-Native Soluble Protein Form Captured from Cell Lysate In one experiment, a recombinant protein comprising a plurality of polypeptides joined to an Fc moiety was expressed in E. coli as an intracellular soluble peptide chain, lysed from harvested and washed cells, isolated from the lysate by affinity chromatography, and then refolded at a concentration of approximately 12 g/L, as described herein.

After the completion of the expression phase, an aliquot of whole fermentation broth was centrifuged and the liquid fraction removed, leaving the cells as a paste. The cells were resuspended in water to approximately 60% of the original volume. The cells were then lysed by means of three passes through a high pressure homogenizer. After the cells were lysed, the lysate pool was mixed in the presence of air for 8-72 hours to allow for dimerization of the peptide chains. Following the dimerization process, the peptide chain of interest was isolated from the lysate pool using a Protein A affinity chromatography column. The Protein A column elution pool was mixed at a ratio of 8 parts Protein A elution material to 2 parts of a refold buffer containing urea (10 M), arginine-HCl (2.5 M), Tris at pH 8.5 (1050 mM), and cysteine (10 mM, 5 mM, or 4 mM) and cystamine (4 mM). The diluted mixture was titrated to pH 8.5 and incubated at approximately 5° C. under nitrogen until a stable pool was achieved (~24 hours.) Yields of desired product of approximately 30-80% were obtained a depending on the redox condition evaluated.

In order to emulate the non-anaerobic conditions similar to those typically present in very large-scale protein production processes several steps were taken. When reaction volumes were less than approximately 15 L the refold vessel headspace was purged with nitrogen to limit the effect oxygen could have in the system. The vessel was then sealed and incubation began.

When reaction volumes were more than approximately 15 L but less than 500 L, the refold buffer was prepared and allowed to equilibrate at approximately 5° C. to achieve a stable oxygen level in the solution (typically 50% to 70% dissolved oxygen, relative to air saturation). Once the refold mixture was formed, the vessel headspace was purged with nitrogen to limit any additional effect oxygen could have in the system, the vessel was sealed and incubation period initiated.

Example 4

High Concentration Refolding from Inclusion Bodies

In one experiment, a recombinant protein comprising a biologically active peptide linked to the C-terminus of the Fc moiety of an IgG 1 molecule via a linker and having a molecular weight of about 57 kDa and comprising 8 disulfide bonds, was expressed in E. coli as inclusion bodies, harvested, washed, concentrated, solubilized, and refolded at a concentration of 6 g/L as described herein.

An aliquot of frozen concentrated inclusion bodies were thawed to room temperature and mixed with an appropriate amount of guanidine and/or urea to generate a denaturant level equivalent to 4-6 M guanidine, which fully denatures the protein. The protein was then reduced with DTT, at 5-20 mM, at pH 8.5, and incubated at room temperature for approximately 1 hour. After the inclusion bodies were dissolved, denatured and reduced, they were diluted into a refold buffer containing urea (1-5 M), arginine-HCl (5-500 mM), glycerol (10-30% w/v), and the identified levels of cysteine and cystamine as determined by the procedure described in Example 2. The final component concentrations are 4 M urea, 150 mM arginine HCl, 20.9% (w/v) glycerol, 2.03 mM cysteine, and 2.75 mM cystamine. The level of dilution was chosen to balance the dilution of the denaturants from the solubilization, maintain the thermodynamic stability of the molecule during refolding, and maintain the highest possible protein concentration in the refold mixture. The diluted mixture was titrated to an alkaline pH (between pH 8 and pH 10) and incubated at 5° C. under non-aerobic conditions until a stable pool was achieved (12-72 hours), as determined by relevant analytical measurements. The resulting process was demonstrated to show stable scalablity from 1 L-scale to 2000 L-scale (see FIG. 3). Yields of desired product of approximately 27-35% were obtained at both scales. The distribution of product related impurities was also maintained within a tight variance (see FIG. 3).

Oxygen mass transfer at small-scale is readily achieved and should be inhibited in order to emulate the relatively poorer mass transfer observed at large-scale, where the volume of refold solution is large relative to the volume of air and surface area present at the surface of a large-scale vessel. Thus, in order to emulate the non-anaerobic conditions similar to those typically present in very large-scale protein production processes several steps were taken. When reaction volumes were less than approximately 15 L the refold buffer was sparged with nitrogen to strip oxygen from the solution, the components were dispensed under a blanket of nitrogen and once the refold mixture was formed, the vessel headspace was purged with nitrogen to limit the effect oxygen could have in the system. The vessel was then sealed and incubation began.

When reaction volumes were more than approximately 15 L but less than 500 L, the refold buffer was prepared and allowed to equilibrate at approximately 5° C. to achieve a stable oxygen level in the solution (typically 50% to 70% dissolved oxygen, relative to air saturation). Once the refold mixture was formed, the vessel headspace was purged with nitrogen to limit any addition effect oxygen could have in the system, the vessel was sealed and the incubation period was initiated.

At scales greater than 500 L the refold buffer was prepared and allowed to equilibrate at approximately 5° C. to achieve a stable oxygen level in the solution (typically 50% to 70% dissolved oxygen, relative to air saturation). Once the refold mixture was formed, the vessel was sealed and the incubation period was initiated.

The protein concentration of the refold mixture was 6 g/L, which is a four-fold enhancement over the recovery of 1.5 g/L obtained using a method other than the method described in this Example. Overall annual process productivity, in one specific manufacturing facility, was calculated to be increased by >930% due to increased volumetric efficiency in the existing facility tanks.

Example 5

Effect of Thiol-Pair Oxidation State on Disulfide Pairings

FIGS. 1a-1f demonstrate that as the thiol-pair ratio is forced to a more oxidizing state (lower thiol-pair ratio), a higher proportion of product species have oxidized amino acid residues and mixed disulfide forms. As the thiol-pair ratio is driven to a more reductive state (higher thiol-pair ratio), this results in lower levels of oxidized amino acid variant species and higher levels of product species with incorrect disulfide pairings or unformed disulfide bonds. As the overall thiol-pair buffer strength is modified, the corresponding optimal thiol-pair ratio is shifted. This effect is similar to how buffer strength modulates the sensitivity of pH to acid and base additions in a buffered solution.

An optimal balance of species was attainable. As shown in FIGS. 1a-1f, there is a clear relationship between thiol-pair buffer strength and thiol-pair ratio that can be identified to maintain the optimal species balance and thus facilitate efficient refolding of low solubility proteins. The ability to control product variant species, such as incorrectly disulfide-bonded species and misfolded species, via modulation of the thiol-pair ratio and thiol-pair buffer strength, enables efficient, effective and reliable subsequent purification processes.

Example 6

Effect of Non-Aerobic Conditions on Refolding Efficiency

Figure 2:
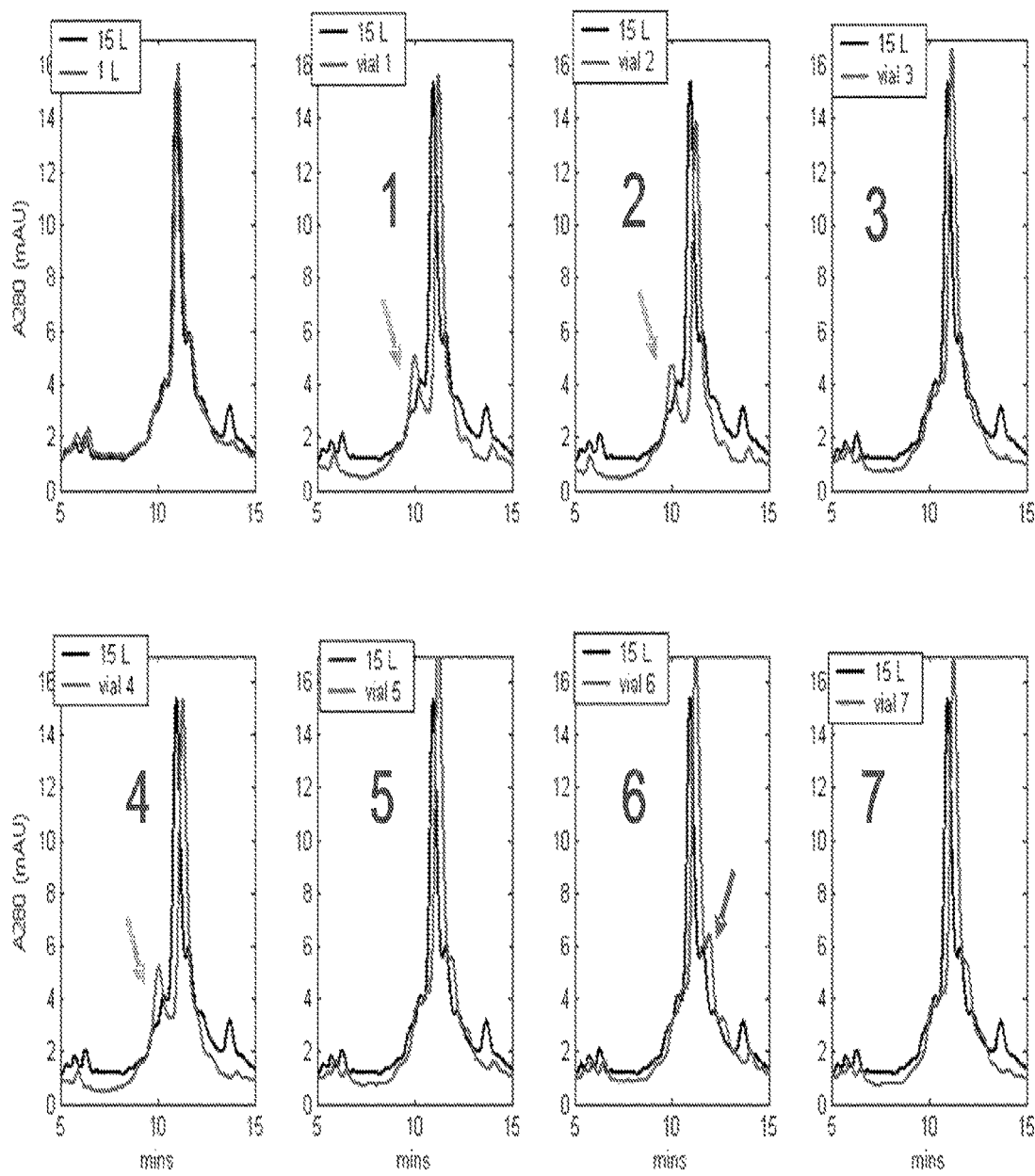
FIG. 2 is a series of plots depicting the effect of the degree of aeration on the species distribution under fixed thiol-pair ratio and thiol-pair buffer strength.
Figure 3:
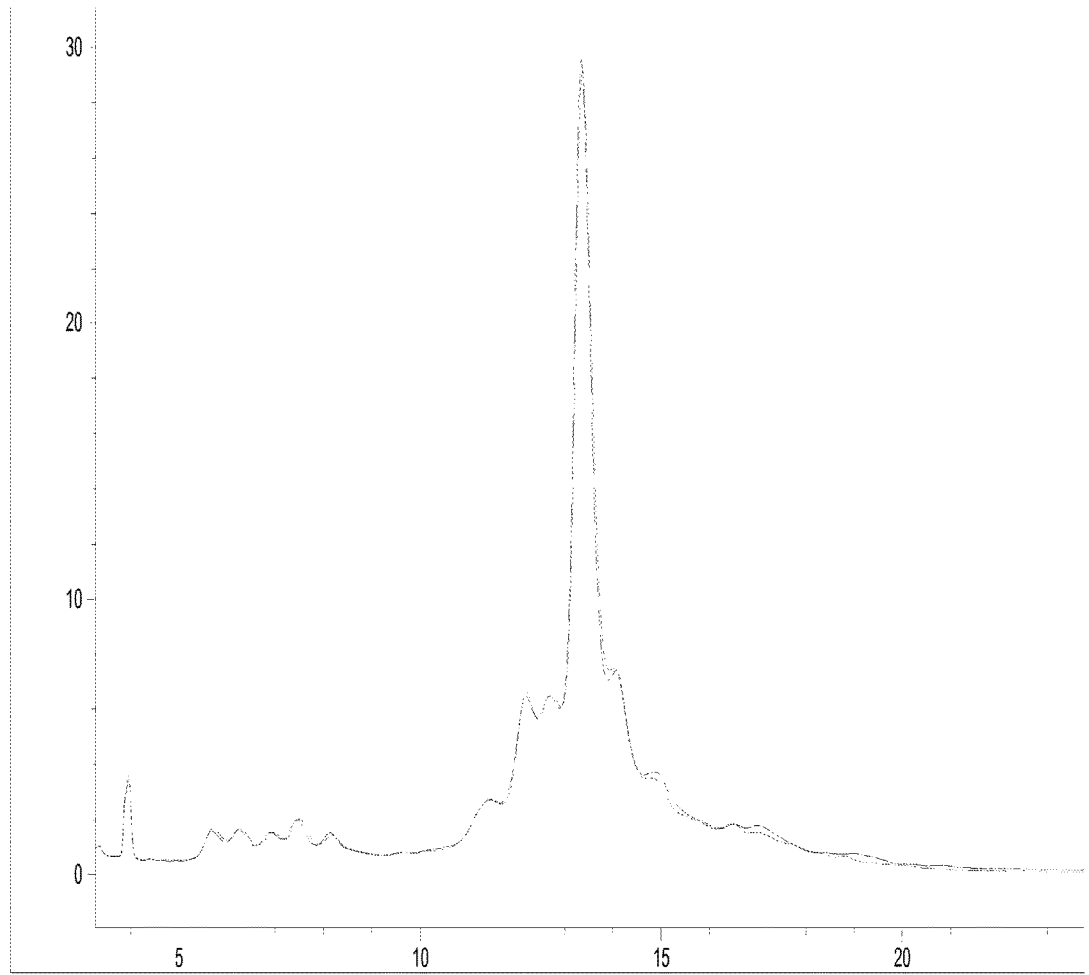
FIG. 3 is an analytical overlay of a chemically controlled, non-aerobic refold performed at 6 g/L and optimized using an embodiment of the described method performed at 1 L and 2000 L.

FIGS. 2 and 3 demonstrate that when the thiol-pair buffer strength is selected appropriately, taking into account the protein concentration and number of cysteine residues in the protein, the sensitivity to external influences, such as oxygen, is significantly reduced. This allows for a non-aerobic refolding condition that is significantly easier to transfer between scales and reactor configurations.

FIG. 2 compares the RP-HPLC analytical species distribution between a 15 L-scale refold and a 20 mL-scale refold under several environmental conditions. For Condition 1 (the trace labeled "1" in FIG. 2), the solubilization chemicals and solutions were dispensed in air and the refold mixture was incubated in air. In Condition 2 solubilization chemicals and solutions were dispensed in air and incubated under nitrogen headspace. In Conditions 3-7 solubilization chemicals and solutions were dispensed under nitrogen overlay conditions and in conditions 3, 5, 6, and 7 solubilization chemicals and solutions were incubated under nitrogen. In Condition 7, the refold solution was also stripped of nitrogen prior to combination with the solubilization solution. In Condition 4 the solubilization chemicals and solutions were incubated under ambient air conditions.

The results shown in FIG. 2 demonstrate that the conditions under which the solubilization chemicals and solutions were dispensed or incubated in the presence of air (i.e., Conditions 1, 2, and 4) do not achieve results that are comparable to the larger-scale control. In Conditions 1, 2 and 4, increased formation of oxidized species (pre-peaks) are observed. The pre-peaks are indicated by arrows in the panels for Conditions 1, 2 and 4.

FIG. 3 compares the RP-HPLC analytical results of an identified condition, achieved as described in Example 2, at 1 L-scale and 2000 L-scale. In this figure, essentially no difference in the distribution of species is detectable. Taken together, FIGS. 2 and 3 demonstrate that when aeration is carefully controlled, the small-scale refold reactions are more predictive of those expected upon scale-up of the refold reaction, facilitating the implementation of large-scale protein refolding processes.

What is claimed is:

1. A method of refolding proteins expressed in a non-mammalian expression system, the method comprising:
   contacting the proteins with a preparation that supports the renaturation of at least one of the proteins to a biologically active form, to form a refold mixture, the preparation comprising:
      at least one ingredient selected from the group consisting of a denaturant, an aggregation suppressor and a protein stabilizer;
      an amount of oxidant; and
      an amount of reductant,
      wherein the amounts of the oxidant and the reductant are related through a thiol-pair ratio and a thiol-pair buffer strength,
      wherein the thiol-pair ratio is in the range of 0.001-100; and
      wherein the thiol-pair buffer strength maintains the solubility of the preparation; and
   incubating the refold mixture so that at least about 25% of the proteins are properly refolded.

2. The method of claim 1, wherein the refold mixture has a protein concentration in a range of 1-40 g/L.

3. The method of claim 1, wherein the refold mixture has a protein concentration of 2.0 g/L or greater.

4. The method of claim 1, wherein the thiol-pair buffer strength is 2 mM or greater.

5. The method of claim 1, wherein the thiol-pair buffer strength is increased proportionally to an increase in a total protein concentration in the refold mixture.

6. The method of claim 1, wherein the thiol-pair buffer strength is decreased proportionally to a decrease in a total protein concentration in the refold mixture.

7. The method of claim 1, wherein the at least one of the proteins is a complex protein.

8. The method of claim 1, wherein the thiol-pair ratio is calculated according to the following equation:

$$\frac{[\text{the reductant}]^2}{[\text{the oxidant}]}.$$

9. The method of claim 1, wherein the thiol-pair buffer strength is calculated according to the following equation:

$$2[\text{the oxidant}] + [\text{the reductant}].$$

10. A method of refolding proteins expressed in a non-mammalian expression system, the method comprising:
  contacting the proteins with a preparation that supports the renaturation of at least one of the proteins to a biologically active form, to form a refold mixture, the preparation comprising:
    at least one ingredient selected from the group consisting of a denaturant, an aggregation suppressor and a protein stabilizer;
    an amount of oxidant; and
    an amount of reductant,
    wherein the amounts of the oxidant and the reductant are related through a thiol-pair ratio and a thiol-pair buffer strength,
    wherein the thiol-pair ratio is in the range of 0.001-100; and
    wherein the thiol-pair buffer strength maintains the solubility of the preparation; and
  incubating the refold mixture so that about 30-80% of the proteins are properly refolded.

11. The method of claim 10, wherein the refold mixture has a protein concentration in a range of 1-40 g/L.

12. The method of claim 10, wherein the thiol-pair buffer strength is 2 mM or greater.

13. The method of claim 10, wherein the refold mixture has a protein concentration of 2.0 g/L or greater.

14. The method of claim 1, wherein:
the thiol-pair ratio is calculated according to the following equation:

$$\frac{[\text{the reductant}]^2}{[\text{the oxidant}]};$$

and
the thiol-pair buffer strength is calculated according to the following equation:

$$2[\text{the oxidant}]+[\text{the reductant}].$$

15. The method of claim 10, wherein:
the thiol-pair ratio is calculated according to the following equation:

$$\frac{[\text{the reductant}]^2}{[\text{the oxidant}]};$$

and
the thiol-pair buffer strength is calculated according to the following equation:

$$2[\text{the oxidant}]+[\text{the reductant}].$$

16. A method of refolding proteins expressed in a non-mammalian expression system, the method comprising:
  preparing a solution comprising:
    the proteins;
    at least one ingredient selected from the group consisting of a denaturant, an aggregation suppressor and a protein stabilizer;
    an amount of oxidant; and
    an amount of reductant,
    wherein the amounts of the oxidant and the reductant are related through a thiol-pair ratio and a thiol-pair buffer strength,
    wherein the thiol-pair ratio is in the range of 0.001-100, and
    wherein the thiol-pair buffer strength maintains the solubility of the solution; and
  incubating the solution so that at least about 25% of the proteins are properly refolded.

17. The method of claim 16, wherein the solution has a protein concentration in a range of 1-40 g/L.

18. The method of claim 16, wherein the solution has a protein concentration of 2.0 g/L or greater.

19. The method of claim 16, wherein the thiol-pair buffer strength is 2 mM or greater.

20. The method of claim 16, wherein the thiol-pair buffer strength is increased proportionally to an increase in a total protein concentration in the solution.

21. The method of claim 16, wherein the thiol-pair buffer strength is decreased proportionally to a decrease in a total protein concentration in the solution.

22. The method of claim 16, wherein the at least one of the proteins is a complex protein.

23. The method of claim 16, wherein the thiol-pair ratio is calculated according to the following equation:

$$\frac{[\text{the reductant}]^2}{[\text{the oxidant}]}.$$

24. The method of claim 16, wherein the thiol-pair buffer strength is calculated according to the following equation:

$$2[\text{the oxidant}]+[\text{the reductant}].$$

25. The method of claim 16, wherein:
the thiol-pair ratio is calculated according to the following equation:

$$\frac{[\text{the reductant}]^2}{[\text{the oxidant}]};$$

and
the thiol-pair buffer strength is calculated according to the following equation:

$$2[\text{the oxidant}]+[\text{the reductant}].$$

26. A method of refolding proteins expressed in a non-mammalian expression system, the method comprising:
  preparing a solution comprising:
    the proteins;
    at least one ingredient selected from the group consisting of a denaturant, an aggregation suppressor and a protein stabilizer;
    an amount of oxidant; and
    an amount of reductant,
    wherein the amounts of the oxidant and the reductant are related through a thiol-pair ratio and a thiol-pair buffer strength,
    wherein the thiol-pair ratio is in the range of 0.001-100, and
    wherein the thiol-pair buffer strength maintains the solubility of the solution; and
  incubating the solution so that about 30-80% of the proteins are properly refolded.

27. The method of claim 26, wherein the solution has a protein concentration in a range of 1-40 g/L.

28. The method of claim 26, wherein the solution has a protein concentration of 2.0 g/L or greater.

29. The method of claim 26, wherein the thiol-pair buffer strength is 2 mM or greater.

30. The method of claim 26, wherein:
the thiol-pair ratio is calculated according to the following equation:

$$\frac{[\text{the reductant}]^2}{[\text{the oxidant}]};$$

and
the thiol-pair buffer strength is calculated according to the following equation:

$$2[\text{the oxidant}]+[\text{the reductant}].$$

* * * * *